(12) United States Patent
Sable et al.

(10) Patent No.: US 8,741,313 B2
(45) Date of Patent: Jun. 3, 2014

(54) POLYPEPTIDE VACCINE AND VACCINATION STRATEGY AGAINST MYCOBACTERIUM

(75) Inventors: Suraj Sable, Atlanta, GA (US); Bonnie B. Plikaytis, Atlanta, GA (US); Thomas M. Shinnick, Atlanta, GA (US); Rama Rao Amara, Decatur, GA (US); Manl Cheruvu, Savannah, GA (US)

(73) Assignees: Emory University, Atlanta, GA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 172 days.

(21) Appl. No.: 12/812,541

(22) PCT Filed: Jan. 12, 2009

(86) PCT No.: PCT/US2009/030754
§ 371 (c)(1),
(2), (4) Date: Oct. 8, 2010

(87) PCT Pub. No.: WO2009/089535
PCT Pub. Date: Jul. 16, 2009

(65) Prior Publication Data
US 2011/0027349 A1 Feb. 3, 2011

Related U.S. Application Data

(60) Provisional application No. 61/020,573, filed on Jan. 11, 2008.

(51) Int. Cl.
*A61K 39/00* (2006.01)
*A61K 39/02* (2006.01)
*A61K 39/04* (2006.01)
*A61K 39/116* (2006.01)
*A61K 45/00* (2006.01)

(52) U.S. Cl.
USPC ............... 424/248.1; 424/178.1; 424/184.1; 424/192.1; 424/203.1; 424/234.1; 424/278.1; 424/282.1

(58) Field of Classification Search
None
See application file for complete search history.

(56) References Cited

U.S. PATENT DOCUMENTS

| | | | |
|---|---|---|---|
| 6,391,318 B1 | 5/2002 | Illum et al. | |
| 6,558,670 B1 | 5/2003 | Friede et al. | |
| 6,630,169 B1 | 10/2003 | Bot et al. | |
| 7,037,510 B2 | 5/2006 | Andersen et al. | |
| 7,288,261 B2 | 10/2007 | Orme et al. | |
| 7,538,206 B2 | 5/2009 | Cole | |
| 2003/0039665 A1 | 2/2003 | Illum et al. | |
| 2004/0009937 A1 | 1/2004 | Chen et al. | |
| 2004/0057963 A1* | 3/2004 | Andersen et al. | 424/190.1 |
| 2004/0171523 A1* | 9/2004 | Marchal et al. | 514/8 |
| 2005/0075298 A1 | 4/2005 | Chen et al. | |
| 2005/0084904 A1* | 4/2005 | Laal et al. | 435/7.1 |
| 2007/0134267 A1 | 6/2007 | Grode et al. | |

FOREIGN PATENT DOCUMENTS

| | | |
|---|---|---|
| KR | 100609813 B1 | 7/2006 |
| KR | 1020070068398 | 6/2007 |
| WO | WO-2006/136162 A2 | 12/2006 |

OTHER PUBLICATIONS

Sable et al., (Vaccine. Feb. 2007. vol. 25(9): 1553-1566. Available online Nov. 15, 2006).*
Sable et al. (Vaccine. 2005. vol. 23:4175-4184).*
Huard et al., (Infect. & Immun. 2003. vol. 71(12):6871-6883).*
Falero-Diaz et al., (Vaccine. 2000. vol. 18:3223-3229).*
Rosenkrands et al., (Infection and Immunity. 1999. vol. 67(11): 5552-5558).*
Sable, S. et al.,Tuberculosis subunit vaccine development: Impact of physicochemical properties of mycobacterial test antigens:, Vaccine, 2006, vol. 25, No. 9; pp. 1553-1566.
Sable, S. et al., Tuberculosis subunit vaccine design: The conflict of antigenicity and immunogenicity, Clinical immunology, 2007; vol. 122; No. 3; pp. 239-251.
Al-Attiyah, R. et al., Cytokine profiles in tuberculosis patients and healthy subjects in response to complex and single antigens of *Mycobacterium tuberculosis*, FEMS Immunol. Med. Microbiol., 2006, vol. 47, pp. 254-261.
Anonymous. 2006. Emergence of *Mycobacterium tuberculosis* with extensive resistance to second-line drugs—worldwide, 2000-2004. Centers for Disease Control and Prevention. MMWR 55:301-305.
Agger, E. M., and P. Andersen. 2002. A novel TB vaccine; towards a strategy based on our understanding of BCG failure. Vaccine 21:7-14.
Andersen, P., and T. M. Doherty. 2005. The success and failure of BCG—implications for a novel tuberculosis vaccine. Nat Rev Microbiol 3:656-662.
Arulanadam, B. P., R. H. Raeder, J. G. Nedrud, D. J. Bucher, J. Le, and D. W. Metzger. 2001. IgA immunodeficiency leads to inadequate Th cell priming and increased susceptibility to influenza virus infection. J Immunol 166:226-231.
Asanuma, H., A. H. Thompson, T. Iwasaki, Y. Sato, Y. Inaba, C. Aizawa, T. Kurata, and S. Tamura. 1997. Isolation and characterization of mouse nasal-associated lymphoid tissue. J Immunol Methods 202:123-131.
Beatty, W. L., and D. G. Russell. 2000. Identification of mycobacterial surface proteins released into subcellular compartments of infected macrophages. Infect Immun 68:6997-7002.
Carpenter, Z. K., E. D. Williamson and J. E. Eyles. 2005. Mucosal delivery of microparticle encapsulated ESAT-6 induces robust cell-mediated response in the lung milieu. J Control Release 104:67-77.

(Continued)

*Primary Examiner* — Ja'Na Hines
(74) *Attorney, Agent, or Firm* — Gifford, Krass, Sprinkle, Anderson & Citkowski, P.C.

(57) ABSTRACT

A vaccine is provided wherein a polypeptide or combination of peptides from *M. tuberculosis* is administered to a subject to elicit an immune response. The polypeptide vaccine is administered as part of a prime-boost strategy with BCG vaccine to increase the immunoprotection in a subject such that prevention or elimination of disease is achieved. Finally, a pharmaceutical package is provided that encompasses a polypeptide vaccine for *M. tuberculosis* that when administered to a subject elicits immunoprotection.

18 Claims, 18 Drawing Sheets

(56) References Cited

OTHER PUBLICATIONS

Castanon-Arreola, M., Y. Lopez-Vidal, C. Espitia-Pinzon, and R. Hernandez-Pando. 2005. A new vaccine against tuberculosis shows greater protection in a mouse model with progressive pulmonary tuberculosis. Tuberculosis (Edinburgh, Scotland) 85:115-126.

Chen, L., J. Wang, A. Zganiacz, and Z. Xing. 2004. Single intranasal mucosal *Mycobacterium bovis* BCG vaccination confers improved protection compared to subcutaneous vaccination against pulmonary tuberculosis. Infect Immun 72:238-246.

D'Souza, S., V. Rosseels, O. Denis, A. Tanghe, N. De Smet F. Jurion, K. Palfliet, N. Castiglioni, A. Vanockelen, C. Wheeler, and K. Huygen. 2002. Improved tuberculosis DNA vaccines by formulation in cationic lipids. Infect Immun 70:3681-3688.

Denis, O., E. Lozes, and K. Huygen. 1997. Induction of cytotoxic T-cell responses against culture filtrate antigens in *Mycobacterium bovis* bacillus Calmette-Guerin-infected mice. Infect Immun 65:676-684.

Di Rosa, F., and R. Pabst. 2005. The bone marrow: a nest for migratory memory T cells. Trends Immunol 26:360-366.

Dietrich, J., C. Andersen, R. Rappuoli, T. M. Doherty, C. G. Jensen, and P. Andersen. 2006. Mucosal administration of Ag85B-ESAT-6 protects against infection with *Mycobacterium tuberculosis* and boosts prior bacillus Calmette-Guerin immunity. J Immunol 177:6353-6360.

Dobos, K. M., K. H. Khoo, K. M. Swiderek, P. J. Brennan, and J. T. Belise. 1996. Definition of the full extent of glycosylation of the 45-kilodalton glycoprotein of *Mycobacterium tuberculosis*, J Bacteriol 178:2498-2506.

Falero-Diaz, G., S. Challacombe, D. Banerjee, G. Douce, A. Boyd, and J. Ivanyi. 2000. Intranasal vaccination of mice against infection with *Mycobacterium tuberculosis*. Vaccine 18:3223-3229.

Fattorini, L., R. Creti, R. Nisini, R. Pietrobono, Y. Fan, A. Stringaro, G. Arancia, O. Serlupi-Crescenzi, E. Iona, and G. Orefici. 2002. Recombinant GroES in combination with CpG oligodeoxynucleotides protects mice against *Mycobacterium avium* infection. J Med Microbiol 51:1071-1079.

Ferraz, J. C., E. Stavropoulos, M. Yang, S. Coade, C. Espitia, D. B. Lowrie, M. J. Colston, amd R. E. Tascon. 2004. A heterologous DNA priming-*Mycobacterium bovis* BCG boosting immunization strategy using mycobacterial Hsp70, Hsp65, and Apa antigens improves protection against tuberculosis in mice. Infect Immun 72:6945-6950.

Giri, P. K., S. B. Sable, I. Verma, and G. K. Khuller. 2005. Comparative evaluation of intranasal and subcutaneous route of immunization for development of mucosal vaccine against experimental tuberculosis. FEMS Immunol Med Microbiol 45:87-93.

Giri, P. K., I. Verma, and G. K. Khuller. 2006. Enhanced immunoprotective potential of *Mycobacterium tuberculosis* Ag85 complex protein based vaccine against airway *Mycobacterium tuberculosis* challenge following intranasal administration. FEMS Immunol Med Microbiol 47:233-241.

Goonetilleke, N. P., H. McShane, C. M. Hannan, R. J. Anderson, R. H. Brookes, and A. V. Hill. 2003, Enhanced immunogenicity and protective efficacy against *Mycobacterium tuberculosis* of bacille Calmette-Guerin vaccine using mucosal administration and boosting with a recombinant modified vaccinia virus Ankara. J Immunol 171:1602-1609.

Grode, L., P. Seiler, S. Baumann, J. Hess, V. Brinkmann, A. Nasser Eddine, P. Mann, C. Goosmann, S. Bandermann, D. Smith, G. J. Bancroft, J. M. Reyrat, D. van Soolingen, B. Raupach, and S. H. Kaufmann. 2005. Increased vaccine efficacy against tuberculosis of recombinant *Mycobacterium bovis* bacille Calmette-Guerin mutants that secrete listeriolysin. J Clin Invest 115:2472-2479.

Grover, A., M. F. Ahmed, B. Singh, I. Verma, P. Sharma, and G. K. Khuller. 2006. A multivalent combination of experimental antituberculosis DNA vaccine based on Ag85B and regions of difference antigens. Microbes Infect / Institut Pasteur 8:2390-2399.

Hagiwara, Y., J. R. McGhee, K. Fujihashi, R. Kobayashi, N. Yoshino, K. Kataoka, Y. Etani, M. N. Kweon, S. Tamura, T. Kurata, Y. Takeda, H. Kiyono, and K. Fujihashi. 2003. Protective mucosal immunity in aging is associated with functional CD4+ T cells in nasopharyngeal-associated lymphoreticular tissue. J Immunol 170:1754-1762.

Haile, M., B. Hamasur, T. Jaxmar, D. Gavier-Widen, M. A. Chambers, B. Sanchez, U. Schroder, G. Kallenius, S. B. Svenson, and A. Pawlowski. 2005. Nasal boost with adjuvanted heat-killed BCG or arabinomannan-protein conjugate improves primary BCG-induced protection in C57BL/6 mice. Tuberculosis (Edinburgh, Scotland) 85:107-114.

Hamasur, B., M. Haile, A. Pawlowski, U. Schroder, A. Williams, G. Hatch, G. Hall, P. Marsh, G. Kallenius, and S. B. Svenson. 2003. *Mycobacterium tuberculosis* arabinomannan-protein conjugates protect against tuberculosis. Vaccine 21:4081-4093.

Horn, C., A. Namane, P. Pescher, M. Riviere, F. Romain, G. Puzo, O. Barzu, and G. Marchal. 1999. Decreased capacity of recombinant 45/47-kDa molecules (Apa) of *Mycobacterium tuberculosis* to stimulate T lymphocyte responses related to changes in their mannosylation pattern. J Biol Chem 274:32023-32030.

Horwitz, M. A., G. Harth, B. J. Dillon, and S. Maslesa-Galic. 2000. Recombinant bacillus calmette-guerin (BCG) vaccines expressing the *Mycobacterium tuberculosis* 30-kDa major secretory protein induce greater protective immunity against tuberculosis than conventional BCG vaccines in a highly susceptible animal model. Proc. Natil Acad Sci U S A 97:13853-13858.

Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte/macrophage colony-stimulating factor. J Exp Med 176:1693-1702.

Kallenius, G., A. Pawlowski, P. Brandtzaeg, and S. Svenson. 2007. Should a new tuberculosis vaccine be administered intranasally? Tuberculosis (Edinburgh, Scotland).

Kamath, A. T., C. G. Feng, MacDonald, H. Briscoe, and W. J. Britton. 1999. Differential protective efficacy of DNA vaccines expressing secreted protein of *Mycobacterium tuberculosis*. Infect Immun 67:1702-1707.

Kaufmann, S. H. 2006. Envisioning future strategies for vaccination against tuberculosis. Nat Rev Immunol 6:699-704.

Kawanishi, H., and J. Kiely. 1989. Immune-related alterations in aged gut-associated lymphoid tissues in mice. Dig Dis Sci 34:175-184.

Kumar, P., R. R. Amara, V. K. Challu, V. K. Chadda, and V. Satchidanandam. 2003. The Apa protein of *Mycobacterium tuberculosis* stimulate gamma interferon-secreting CD4+ and CD8+ T cells from purified protein derivative-positive individuals and affords protection in a guinea pig model. Infect Immun 71:1929-1937.

Kuroda, K., E. J. Brown, W. B. Telle, D. G. Russell, and T. L. Ratliff. 1993. Characterization of the internalization of bacillus Calmette-Guerin by human bladder tumor cells. J Clinical Invest 91:69-76.

Lefrancois, L., and D. Masopust. 2002. T cell immunity in lymphoid and non-lymphoid tissues. Curr Opin Immunol 14:503-508.

McShane, H., A. A. Pathan, C. R. Sander, S. M. Keating, S. C. Gilbert, K. Huygen, H. A. Fletcher, and A. V. Hill. 2004. Recombinant modified vaccinia virus Ankara expressing antigen 85A boosts BCG-primed and naturally acquired antimycobacterial immunity in humans. Nat Med 10:1240-1244.

Mustafa, A. S., K. E. Lundin, and F. Oftung. 1993. Human T cells recognize mycobacterial heat shock proteins in the context of multiple HLA-DR molecules: studies with healthy subjects vaccinated with *Mycobacterium bovis* BCG and *Mycobacterium leprae*. Infect Immun 61:5294-5301.

Parida, S. K., K. Huygen, B. Ryffel, and T. Chakraborty. 2005. Novel Bacterial Delivery System with Attenuated *Salmonella typhimurium* Carrying Plasmid Encoding Mtb Antigen 85A for Mucosal Immunization: Establishment of Proof of Principle in TB Mouse Model. Ann N Y Acad Sci 1056:366-378.

Quiding-Jarbrink, M., I. Nordstrom, G. Granstrom, A. Kilander, M. Jertborn, E. C. Butcher, A. I. Lazarovits, J. Holmgren, and C. Czerkinsky. 1997. Differential expression of tissue-specific adhesion molecules on human circulating antibody-forming cells after systemic, enteric, and nasal immunizations. A molecular basis for the compartmentalization of effector B cell responses. J Clin Invest 99:1281-1286.

(56) References Cited

OTHER PUBLICATIONS

Reinhardt, R. L., A. Khoruts, R. Merica, T. Zell, and M. K. Jenkins, 2001. Visualizing the generation of memory CD4 T cells in the whole body. Nature 410:101-105.
Rodriguez, A., A. Tjarnlund, J. Ivanji, M. Singh, I. Garcia, A. Williams, P. D. Marsh, M. Troye-Blomberg, and C. Fernandez. 2005. Role of IgA in the defense against respiratory infections IgA deficient mice exhibited increased susceptibility to intranasal infection with *Mycobacterium bovis* BCG. Vaccine 23:2565-2572.
Romain, F., C. Horn, P. Pescher, A. Namane, M. Riviere, G. Puzo, O. Barzu, and G. Marchal. 1999. Deglycosylation of the 45/47-kilodalton antigen complex of *Mycobacterium tuberculosis* decreases its capacity to elicit in vivo or in vitro cellular immune responses. Infect Immun 67:5567-5572.
Romain, F., A. Laqueyrerie, P. Militzer, P. Pescher, P. Chavarot, M. Lagranderie, G. Auregan, M. Gheorghiu, and G. Marchal. 1993. Identification of a *Mycobacterium bovis* BCG 45/47-kilodalton antigen complex, an immunodominant target for antibody response after immunization with living bacteria. Infect Immun 61:742-750.
Rook, G. A., K. Dheda, and A. Zumla. 2005. Do successful tuberculosis vaccines need to be immunoregulatory rather than merely Th1-boosting? Vaccine 23:2115-2120.
Rudin, A., E. L. Johansson, C. Bergquist, and J. Holmgren. 1998. Differential kinetics and distribution of antibodies in serum and nasal and vaginal secretions after nasal and oral vaccination of humans. Infect Immun 66:3390-3396.
Sable, S. B., D. Goyal, I. Verma, D. Behera, and G. K. Khuller. 2007. Lung and blood mononuclear cell responses of tuberculosis patients to mycobacterial proteins. Eur Respir J 29:337-346.
Sable, S. B., I. Verma, and G. K. Khuller. 2005. Multicomponent antituberculous subunit vaccine based on immunodominant antigens of *Mycobacterium tuberculosis*. Vaccine 23:4175-4184.
Sereinig, S., M. Stukova, N. Zabolotnyh, B. Ferko, C. Kittel, J. Romanova, T. Vinogradova, H. Katinger, O. Kiselev, and A. Egorov. 2006. Influenza virus NS vectors expressing the *Mycobacterium tuberculosis* ESAT-6 protein induce CD4+ Th1 immune response and protect animals against tuberculosis challenge. Clin Vaccine Immunol 13:898-904.
Silva, C. L., M. F. Silva, R. C. Pietro, and D. B. Lowrie. 1994. Protection against tuberculosis by passive transfer with T-cell clones recognizing mycobacterial heat-shock protein 65. Immunology 83:341-346.
Skeiky, Y. A., M. R. Alderson, P. J. Ovendale, J. A. Guderian, L. Brandt, D. C. Dillon, A. Campos-Neto, Y. Lobet, W. Dalemans, I. M. Orme, and S. G. Reed. 2004. Differential immune responses and protective efficacy induced by components of a tuberculosis polyprotein vaccine, Mtb72F, delivered as naked DNA or recombinant protein. J Immunol 172:7618-7628.
Smith, C., and C. Cheers. 2005. Synergism between active listeriolysin O and dimethyldioctadecylammonium bromide to activate CD8(+) T cells. Vaccine 23:4481-4488.
Sullivan, V. J., J. A. Mikszta, P. Laurent, J. Huang, and B. Ford. 2006. Noninvasive delivery technologies: respiratory delivery of vaccines. Expert Opin Drug Deliv 3:87-95.
Takahashi, H., K. Sasaki, M. Takahashi, N. Shigemori, S. Honda, H. Arimitsu, S. Ochi, N. Ohara, and T. Tsuji. 2006. Mutant *Escherichia coli* enterotoxin as a mucosal adjuvant induces specific Th1 responses of CD4+ and CD8+ T cells to nasal killed-bacillus calmette-guerin in mice. Vaccine 24:3591-3598.
Van Savage, J., M. D. Decker, K. M. Edwards, S. H. Sell, and D. T. Karzon. 1990. Natural history of pertussis antibody in the infant and effect on vaccine response. J Infect Dis 161:487-492.
Wang, J., L. Thorson, R. W. Stokes, M. Santosuosso, K. Huygen, A. Zganiacz, M. Hitt, and Z. Xing. 2004. Single mucosal, but not parenteral, immunization with recombinant adenoviral-based vaccine provides potent protection from pulmonary tuberculosis. J Immunol 173:6357-6365.
Weinrich Olsen, A., L. A. Van Pinxteren, L. Meng Okkels, P. Birk Rasmussen, and P. Andersen. 2001. Protection of mice with a tuberculosis subunit vaccine based on a fusion protein of antigen 85b and esat-6. Infect Immun 69:2773-2778.
Williams, A., R. Reljic, I. Naylor, S. O. Clark, G. Falero-Diaz, M. Singh, S. Challacombe, P. D. Marsh, and J. Ivanyi. 2004. Passive protection with immunoglobulin A antibodies against tuberculous early infection of the lungs. Immunology 111:328-333.
Worku, S., and D. F. Hoft. 2003. Differential effects of control and antigen-specific T cells on intracellular mycobacterial growth. Infect Immun 71:1763-1773.
Zhao, W., J. S. Schorey, M. Bong-Mastek, J. Ritchey, E. J. Brown, and T. L. Ratliff. 2000. Role of a bacillus Calmette-Guerin fibronectin attachment protein in BCG-induced antitumor activity. Int J Cancer 85:83-88.
Andersen. 2007. The combined CTA1-DD/ISCOMs vector is an effective intranasal adjuvant for boosting prior *Mycobacterium bovis* BCG immunity to *Mycobacterium tuberculosis*. Infection and immunity 75:408-416.
Brandt, L., M. Elhay, I. Rosenkrands, E. B. Lindblad, and P. Andersen. 2000. ESAT-6 subunit vaccination against *Mycobacterium tuberculosis*. Infection and immunity 68:791-795.
Fine, P. E. 2001. BCG: the challenge continues. Scandinavian journal of infectious diseases 33:243-245.
Fine, P. E. 1995. Variation in protection by BCG: implications of and for heterologous immunity. Lancet 346:1339-1345.
Haile, M., U. Schroder, B. Hamasur, A. Pawlowski, T. Jaxmar, G. Kallenius, and S. B. Svenson. 2004. Immunization with heat-killed *Mycobacterium bovis* bacille Calmette-Guerin (BCG) in Eurocine L3 adjuvant protects against tuberculosis. Vaccine 22:1498-1508.
Hesseling, A. C., B. J. Marais, R. P. Gie, H. S. Schaaf, P. E. Fine, P. Godfrey-Faussett, and N. Beyers. 2007. The risk of disseminated Bacille Calmette-Guerin (BCG) disease in HIV-infected children. Vaccine 25:14-18.
Lim, J. H., H. K. Kim, K. S. Lee, E. K. Jo, C. H. Song, S. B. Jung, S. Y. Kim, J. S. Lee, T. H. Paik, and J. K. Park. 2004. Identification of the new T-cell-stimulating antigens from *Mycobacterium tuberculosis* culture filtrate. FEMS microbiology letters 232:51-59.
Oganesyan, N., S. H. Kim, and R. Kim. Sep. 2004. On-column protein refolding for crystallization. PharmGenomics: 22-25.
Orme, I. M. 2006. Preclinical testing of new vaccines for tuberculosis: a comprehensive review. Vaccine 24:2-19.
Sable, S. B., M. Kalra, I. Verma, and G. K. Khuller. 2007. Tuberculosis subunit vaccine design: the conflict of antigenicity and immunogenicity. Clinical immunology (Orlando, Fla 122:239-251.
Sable, S. B., R. Kumar, M. Kalra, I. Verma, G. K. Khuller, K. Dobos, and J. T. Belisle. 2005. Peripheral blood and pleural fluid mononuclear cell responses to low-molecular-mass secretory polypeptides of *Mycobacterium tuberculosis* in human models of immunity to tuberculosis. Infection and immunity 73:3547-3558.
Sable, S. B., I. Verma, D. Behera, and G. K. Khuller. 2005. Human immune recognition-based multicomponent subunit vaccines against tuberculosis. Eur Respir J 25:902-910.
Santosuosso, M., S. McCormick, X. Zhang, A. Zganiacz, and Z. Xing. 2006. Intranasal boosting with an adenovirus-vectored vaccine markedly enhances protection by parenteral *Mycobacterium bovis* BCG immunization against pulmonary tuberculosis. Infection and immunity 74:4634-4643.
Xu, Y., Zhu, B., Wang, Q., Chen, J., Y., Wang, J., Wang, H., Wang, B., and Wang,, H. 2007 Recombinant BCG coexpressing Ag85B, ESAT-6 and mouse-IFN-γ Confers effective protection against *Mycobacterium tuberculosis* in C57BL/6 mice FEMS Immunology and Medical Microbiology, 51:480-487.
Ferraz, et al.; A Heterologous DNA Priming-*Mycobacterium bovis* BCG Boosting Immunization Strategy Using Mycobacterial Hsp70, Hsp65, and Apa Antigens Improves Protection against Tuberculosis in Mice; 2004; Infection and Immunity; pp. 6945-6950.
Romain et al.; Deglycosylation of the 45/47-Kilodalton Antigen Complex *Mycobacterium tuberculosis* Decreases its Capacity to Elicit in Vivo or In Vitro Cellular Immune Responses; 1999; Infection and Immunity; pp. 5567-5572.
Santosuosso et al.; Intranasal Boosting with an Adenovirus-Vectores Vaccine Markedly Enhances Protection by Parenteral *Mycobacterium bovis* BCG Immunization against Pulmonary Tuberculosis; 2006; Infection and Immunity; pp. 4634-4643.

(56) References Cited

OTHER PUBLICATIONS

Skinner et al.; A DNA Prime-*Mycobacterium bovis* BCG Boost Vaccination Strategy for Cattle Induces Protection against Bovine Tuberculosis; 2003; Infection and Immunity; pp. 4901-4907.

Skinner et al.; The Order of Prime-Boost Vaccination of Neonatal Calves with *Mycobacterium bovis* BCG and a DNA Vaccine Encoding Mycobacterial Proteins Hsp65, Hsp70, and Apa Is Not Critical for Enhancing Protection against Bovine Tuberculosis; 2005; Infection and Immunity; pp. 4441-4444.

Ragas et al.; The *Mycobacterium tuberculosis* Cell-surface Glycoprotein Apa as a Potential Adhesin to Colonize Target Cells via the Innate Immune System Pulmonary C-type Lectin Surfactant Protein A; 2007; vol. 282, No. 8; Journal of Biological Chemistry; pp. 5133-5142.

Hogarth et al.; Protective efficacy induced by *Mycobacterium bovis* bacille Calmette-Guèrin can be augmented in an antigen independent manner by use of non-coding plasmid DNA; Elsevier, Vaccine 24 (2006) pp. 95-101.

Pitarque et al.; Deciphering the molecular bases of *Mycobacterium tuberculosis* binding to the lectin DC-SIGN reveals an underestimated complexity; 2005; Biochem J.; pp. 615-624.

Gevorkian et al.; Peptide mimotopes of *Mycobacterium tuberculosis* carbohydrate immunodeterminants; 2005; Biochemistry Society; pp. 411-417.

* cited by examiner

POLYPEPTIDE VACCINE AND VACCINATION STRATEGY AGAINST MYCOBACTERIUM

GOVERNMENT INTEREST

The invention described herein may be manufactured, used and licensing by or for the United States Government.

CROSS-REFERENCE TO RELATED APPLICATIONS

This application is the U.S. national phase of PCT/US2009/030754 filed Jan. 12, 2009, which claims priority of U.S. Provisional Patent Application Ser. No. 61/020,573 filed Jan. 11, 2008, which is incorporated herein by reference.

FIELD OF THE INVENTION

The present invention relates generally to the field of recombinant vaccines and methods of vaccination. More specifically the present invention relates to recombinant *M. tuberculosis* protein administration for use in a prime-boost immunization strategy.

BACKGROUND OF THE INVENTION

Each year 8 to 10 million people worldwide develop tuberculosis. Globally the incidence of tuberculosis is growing at a rate of 1% a year primarily due to rapid increase in disease prevalence in Africa. In other regions successful control efforts have begun to stabilize disease incidence. Nevertheless, approximately 2,000,000,000 people, equal to one-third of the world's population, are estimated to be infected with *Mycobacterium tuberculosis* bacilli, the microbes that cause TB. (World Health Organization 2006 Tuberculosis Facts).

The need to find new treatments or vaccination strategies for tuberculosis is stressed by the increasing worldwide HIV infection rate such that, presently, 250,000 TB deaths are HIV associated. Tuberculosis itself is the second largest killer of mankind with more than 2 million deaths occurring worldwide annually (World Health Organization 2006 Tuberculosis facts). The attenuated *Mycobacterium Bovis bacillus* Calmette-Guerin (BCG) vaccine is the only tuberculosis vaccine currently licensed for human use. The BCG vaccine is effective against severe pediatric and extra-pulmonary forms of tuberculosis. However, protection against adult pulmonary tuberculosis in developing countries is poor, with adult protection varying between 0 to 80% (Fine P. E. M., *Lancet* 2000; 346:1339-1345). The variable efficacy of tuberculosis vaccination appears to be geographically centered. For example in the United Kingdom approximately 75% protection has been observed (Hart P. D. and Sutherland I., *BMJ*, 1977; 2, 293-295). In contrast, clinical studies in India and Malawi failed to show consistent protection against pulmonary tuberculosis (Fine, P E, et al., *Scand J Infec Dis*, 2001; 33:243-45; Ponnighaus J. M., *Lancet*, 1992; 339:636-639).

As the only effective vaccine for TB is the BCG vaccine, current research efforts are focused on improving BCG efficacy (Dietrich G., *Vaccine*, 2003; 21:667-670). For example, recombinant BCG vaccine over expressing fusion protein of the antigen Ag85B, the early secreted antigen (ESAT-6) and IFN-γ increased specific antibody titers and cellular immune responses relative to standard BCG vaccine, recombinant BCG vaccine expressing Ag85B alone, or recombinant BCG vaccine expressing a fusion protein of Ag85B and ESAT-6 (Xu Y., *FEMS Immunology and Medical Microbiology*, 2007; 51:480-487). ESAT-6, a protein produced by virulent *Mycobacterium tuberculosis*, is absent in standard BCG vaccine strains and is currently undergoing intense study as a potential vaccine subunit against tuberculosis. For example, DNA vaccines encoding ESAT-6 combined with immunization with BCG in mice subsequently challenged with tuberculosis H37Rv showed improved ESAT-6 specific interferon gamma (Fan X., Scandinavian *Journal of Immunology* Oct. 4, 2007; 66:523-528).

In addition to studies of new subunit vaccines, prime-boost strategies are currently under investigation as a method of improving BCG immunogenicity (Goonetilleke N. P., *Journal of Immunology* 2003; 171:1602-1609; Kaufmann S. H., *Nature Reviews Immunology* 2001; 1:20-30). Prime-boost strategies commonly employ DNA vaccines. For example, when a DNA vaccine expressing Ag85B was administered in a murine *M. tuberculosis* model followed by boosting with BCG vaccine, improved protective efficacy over BCG vaccine alone was observed (Feng C. G., *Infectious Immunology* 2001; 69:4174-4176). Similarly, DNA injection encoding the *M. tuberculosis* proteins Apa, HSP-65 and HSP-70 subsequently followed by conventional BCG vaccination also improved protection against tuberculosis challenge in mice (Ferraz, *Infection and Immunity* 2004; 72:6945-6950).

Traditional immunizations are generally administered via an intramuscular or subcutaneous route. However, tuberculosis is primarily a respiratory disease. Thus, protection against infection and subsequent eradication of disease may best be accomplished by direct administration to the respiratory mucosa (Kallenius, et al. *Tuberculosis* (Edinb), 2007; 87:257-66). Intranasal vaccination may have advantages over other routes of administration such as, intranasal vaccination is not influenced by a preformed systemic immunity whereas parenteral vaccination is less effective in individuals with preexisting antibodies (van Savage J. M., *Journal of Infectious Disease* 1990; 161:487-492).

Circumventing the existence of preexisting antibodies is important in geographical regions where an improved vaccine against tuberculosis is most needed. Prior Th2 background immunity resulting from prior exposure to helminthes and saprophytic mycobacteria has been suggested to decrease the ability of BCG vaccine in inducing immunoprotection (Rook, *Vaccine*, 2005; 23:2115-2120). Further, it is envisaged that intranasal vaccination might be effective in preventing *M. tuberculosis* infections in the host (Kauffman S H., *Nature Reviews of Immunology* 2006; 6:699-704). Animal studies of intranasal vaccination showed increased protective efficacy as compared to subcutaneous route of vaccination (Giri, P K. et al. *FEMS Immunology and Medical Microbiology*, 2005; 45:87-93; Chen, L. et al. *Infection and Immunity*, 2004; 72:238-246).

While studies of live or killed BCG vaccine, protein subunit vaccines, recombinant bacterial vector vaccines, plasma DNA vaccines or combinatorial immunization approaches in both human and animal systems have been subjected to preliminary study, little is known as to which method produces the most robust immune response and the greatest level of protection in the subject. Further, detail concerning immune response characteristics induced by each vaccine type is yet to be fully elucidated. The increased prevalence of tuberculosis infection and increased resistance, particularly in the developing world, creates a need for an improved tuberculosis vaccine and vaccination strategy.

SUMMARY OF THE INVENTION

A vaccine is provided that increases an immune response in a subject wherein the vaccine includes at least one *M. tuber-* culosis polypeptide wherein the polypeptide is optionally Ag85A, Ag85B, MPT-64, Pst-S1, Apa, GroES, GroEL, Dnak, CFP-10, Rv0831c, and Rv1324, portions thereof, combinations thereof, or multiples thereof. These recombinant proteins are optionally purified in their natural form or they further comprise a tag suitable for increasing purification. The M. tuberculosis polypeptides are optionally recombinant.

An inventive vaccine optionally contains an emulsion. Suitable emulsification agents include supramolecular biovectors (SMBV), nanoparticles, liposomes, or combinations thereof.

An inventive vaccine optionally contains an adjuvant. Suitable adjuvants illustratively include dimethyl dioctadecylammonium bromide (DDA); monophosphoryl lipid A (MPL); LTK63, lipophilic quaternary ammonium salt-DDA, DDA-MPL, aluminum salts, aluminum hydroxyide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles illustratively including calcium phosphate nanoparticles, combination of soybean oil, emulsifying agents, and ethanol to form a nanoemulsion; AS04, ZADAXIN, or combinations thereof.

Also provided is a process of increasing an immune response in a subject wherein an *M. tuberculosis* polypeptide is administered to the subject. Administration is optionally via routes including intradermal, transdermal, subcutaneous, intramuscular, intranasal, aerosolized, oral, sublingual, intravaginal, per-rectal, intravenous, intramucosal, or other methods of delivery known in the art. The process of increasing an immune response optionally employs administering to a subject a second vaccine which is optionally Ag85A, Ag85B, MPT-64, Pst-S1, Apa, GroES, GroEL, Dnak, CFP-10, Rv0831c and Rv1324 or combinations thereof, epitopes of above mentioned polypeptides or peptides thereof. Optionally the administration of a BCG vaccine occurs prior to the administration of a recombinant tuberculosis polypeptide. Alternatively administration of a BCG vaccine might occur subsequent to administration of a recombinant tuberculosis polypeptide or optionally administration of a BCG vaccine occurs simultaneously to the administration of a recombinant tuberculosis polypeptide(s), epitope(s) or peptide(s). The BCG vaccine is optionally recombinant (expressing one or more above mentioned polypeptides) or natural. Furthermore the administration of either a BCG vaccine and/or a recombinant tuberculosis polypeptide occurs prior to, concurrent with, or after the subject is exposed to mycobacterium infections or developed a disease.

Also provided is a pharmaceutical package comprising at least one polypeptide selected from the group comprising Ag85A, Ag85B, MPT-64, Pst-S1, Apa, GroES, GroEL, Dnak, CFP-10, Rv0831c and Rv1324 or combinations thereof. Also an emulsification agent and an adjuvant. The emulsification agent is optionally a dimethyl dioctadecylammonium bromide. Optionally the adjuvant is monophosphoryl lipid A.

DETAILED DESCRIPTION OF THE PREFERRED EMBODIMENTS

Figure 1:
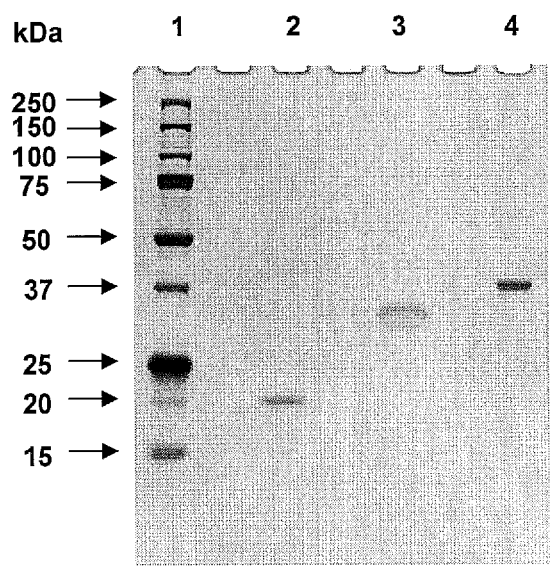
FIG. 1 represents an SDS-PAGE (4-20% gradient gel) of purified new recombinant *M. tuberculosis* proteins processed by silver stain wherein lane 1 represents molecular weight markers, lane 2 is Rv0164, lane 3 is Rv0831c, and lane 4 is Rv1324.
Figure 2:
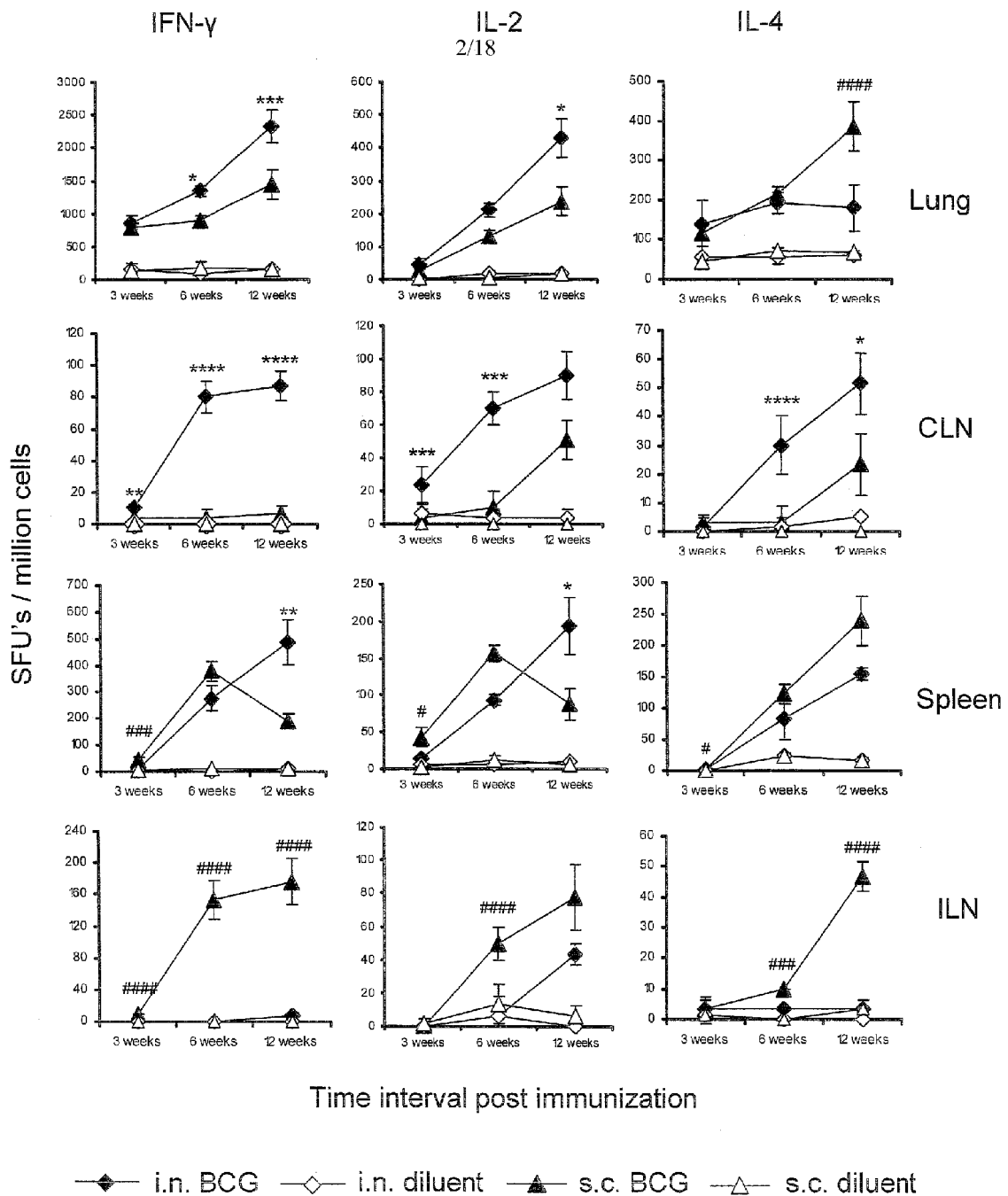
FIG. 2 represents the kinetics of T-cell responses induced by intranasal or subcutaneous BCG vaccination.

The increased prevalence of HIV increases the need for an *M. tuberculosis* vaccine that has efficacy in both pediatric and adult patients in the developed and developing worlds. The instant invention has utility as a new vaccine against *Mycobacterium*.

To answer the wide range of BCG vaccine efficacy against tuberculosis, a novel inventive strategy is provided to boost the immune response generated following administration of a BCG vaccine. Toward this end, secreted proteins of *M. tuberculosis* represent a valuable source of antigens for use in boosting the efficacy of BCG vaccine. The instant invention provides a vaccine that used alone or in conjunction with BCG, increases the immune response of a subject. In a preferred embodiment the instant invention utilizes at least one *M. tuberculosis* polypeptide. Polypeptides suitable in the instant invention include any polypeptide expressed by virulent *M. tuberculosis* within a subject. Polypeptides suitable for use in the instant invention optionally include Ag85A, Ag85B, MPT-64, Pst-S1, Apa, GroES, GroEL, Dnak, CFP-10, Rv0831c and Rv1324, portions thereof, combinations thereof, or multiples. Multiples thereof illustratively mean more than one polypeptide sequence type or more than one copy of a single polypeptide sequence. Polypeptides suitable in the instant invention are optionally recombinant or naturally derived.

Preferably polypeptides suitable in the instant invention are recombinant and obtained by methods known in the art. Illustratively, a nucleotide sequence is cloned into a plasmid which is transfected into *E. coli* and expressed. To ease purification procedures the expressed polypeptides from *E. coli* optionally include a tag sequence. Illustrative examples of tags suitable for use in the instant invention include polyhistidine, CBP, CYD (covalent yet dissociable NorpD peptide), strep-2, FLAG, HPC or heavy chain of protein C peptide tag, or GST and MBP protein fusion tag systems. It is appreciated that other tag systems are similarly operable. In a preferred embodiment recombinant polypeptides are expressed in *E. coli* and purified using an affinity tag system followed by enzymatic cleavage of the tag such as by incorporating a factor Xa, thrombin, or other enzyme cleavage site in the expressed polypeptide. Methods of tag cleavage are known in the art and any effective method is appreciated to be suitable for use in the instant invention.

In a preferred embodiment a multi-component vaccine is employed. The multi-subunit vaccine optionally contains a set of individual polypeptides or a single or family of fusion proteins wherein each of the proteins optionally represents a single protein expressed by virulent *M. tuberculosis*. Preferably a nine polypeptide vaccine is employed. It is appreciated that each individual antigen or polypeptide is individually suitable for use in the instant invention. Unexpectedly, administration of a multi-component vaccine increases the immunogenicity of each of the individual components. Thus, the preferred embodiment of a nine subunit vaccine demonstrates synergistic immunogenicity.

The term subject is illustratively a living organism capable of mounting an immune response to challenge from a vaccine. Non-limiting examples of a subject include a human, any lower primate, dog, cat, rabbit, rat, mouse, guinea pig, pig, hamster, horse, donkey, cattle, possum, badger, goat, or other mammals or non-mammals.

The term immune response is illustratively any alteration of a subject's immune system in response to challenge from a vaccine, infectious or otherwise foreign organism, tissue, cell, antigen, antibody, nucleotide strand, or other immune stimulating substance recognized in the art. Non-limiting examples of immune responses include in vitro secretion of IL-2, IL-4, or IFN-γ in $CD4^+$ or $CD8^+$ T-cells; protection from challenge after *M. tuberculosis* H37Rv or other infectious organism; alteration in nitrite levels; Th1 and Th2 cytokine responses in various immune compartments; alteration in allotype and isotype antibody levels; in vitro recognition of antigen; B-cell responses; inhibition of growth of *M. tuberculosis* bacilli in infected macrophages; survival; or other response known in the art.

The term polypeptide is illustratively a chain of two or more amino acid residues. In a preferred embodiment, a polypeptide suitable for use in the instant invention is the amino acid sequence for Rv1860 (Apa) protein, whole recombinant or natural protein, mutants thereof, portions, epitopes or peptides thereof, homologs thereof, or the Apa sequence combined with other peptide sequences(s). The Apa sequence is found at accession number YP_177849.

Preferably, the inventive vaccine is a multi-component vaccine. A multi-component vaccine illustratively includes nine polypeptide antigens such as Ag85A, Ag85B, MPT-64, Pst-S1, Apa, GroES, GroEL, DnaK, and CFP-10. Representative *Mycobacterium tuberculosis* H37Rv polypeptides operative as candidates for inclusion in a vaccine along with their respective nucleotide sequences:

Ag 85 A (Rv3804c): Gene ID: 886132; protein ID: NP_218321

Ag 85 B (Rv1886c): Gene ID: 885785; protein ID: NP_216402

MPT-64 (Rv1980c): Gene ID: 885925; protein ID: NP_216496

Pst-S1 (Rv0934): Gene ID: 885724; protein ID: YP_177770

Apa (Rv1860): Gene ID: 885896; protein ID: YP_177849

GroES (Rv3418c): Gene ID: 887583; protein ID: NP_217935

GroEL (Rv0440): Gene ID: 886354; protein ID: NP_214954

Dnak (Rv0350): Gene ID: 885946; protein ID: NP_214864

CFP-10 (Rv3874): Gene ID: 886194; protein ID: NP_218391
CFP-31 (Rv0831c): Gene ID: 885349; protein ID: NP_215346
CFP-32 (Rv1324): Gene ID: 886897; protein ID: NP_215840
MTSP-17/CFP-15 (Rv0164): Gene ID: 886267; protein ID: YP_177617

The polypeptides are preferably from *M. tuberculosis* laboratory strains or clinical isolates but can also be from *M. bovis, M. bovis* BCG, *M. avium, M. paratuberculosis, M. smegmatis, M. ulcerans* or other *Mycobacterium* origin. The vaccine is optionally comprised of equal molar concentrations of each antigen, but it is appreciated that unique molar concentrations of each antigen are also suitable in the instant invention. An exemplary vaccine would deliver a total of 90 μg of recombinant antigen mixture per dose comprised of 10 μg of each antigen to a small subject or up to or beyond 1000 μg of each antigen to a human subject. The vaccines are administered in a manner compatible with the dosage formulation, and in such amount as will be prophylactically, therapeutically effective and immunogenic. The quantity to be administered depends on the subject to be treated, including, e.g. the capacity of the individual's immune system to mount an immune response, and the degree of protection desired. Suitable dosage ranges are of the order of several hundred micrograms active ingredient per vaccination with a preferred range from about 0.1 to 1000 μg. Suitable regimens for initial administration and booster shots are also variable but are typified by an initial administration followed by subsequent inoculations or other administrations. The dosage of vaccine will depend on the route of administration and will vary according to the age of the person to be vaccinated and, to a lesser degree, the size of person to be vaccinated.

Surprisingly, intranasal (i.n.) delivery of the above cited multi-subunit vaccine results in lung specific immune responses to each of nine individual antigens. The recognition level of each antigen is unique with the level of IFN-γ secreting cells ordered from:

Apa>MPT-64>DnaK>Pst-S1>GroEL>GroES>Ag85A>Ag85B>CFP-10.

This antigen recognition pattern was also observed in other immune compartments. However, a multiplexed microsphere based cytokine immunoassay showed the greatest response to Ag85A, Ag85B, and Pst-S1 when IL-2 levels were measured. (Table 2.)

In a preferred embodiment a vaccine contains a single polypeptide antigen. Preferably, the antigen is the mycobacterial Apa secretion protein also known as the 45/47-kDa protein complex, or as the protein from gene modD. (Romain, F. et al., *Infect. Immun.,* 1993; 61:724-750.) Apa is secreted as a glycosylated protein with nine glycoforms. (Horn, C., et al., *J. Biol. Chem.,* 1999; 274:32023-32030.) Prior studies demonstrated that glycosylation of Apa is required for antigenicity in vitro and in vivo. (Romain, R, et al., *Infect Immun,* 1999; 67:5567-5572). These authors provide three possible explanations for the requirement of glycosylation in eliciting an immune response. First, glycopeptide specific responses have been reported when immunizing with other glycopeptides implying that both the peptide backbone and the glycosylation interact with the T-lymphocyte receptor (Carbone, F R, and Gleeson P A, *Glycobiology,* 1997; 7:725-730; Deck B, et al., *J Immunol,* 1995; 155:1074-1078; Haurum, J S, et al., *J Exp Med,* 1994; 180:739-744). Second, the responsible receptors for eliciting immune responses may be nonspecific in nature such that mannoslyation of many antigens are recognizable by a single receptor type. (Stahl, P D, and Ezekowitz, R A B, *Curr Opin Immunol,* 1998; 10:50-55). Finally, the presence or absence of glycosylation could alter the uptake or processing of such molecules by macrophages or dendritic cells. Antigenicity of Apa is believed to be related to the presence of glycosylation. However, the effect of glycosylation on T and B cell immunogenicity of APA has not been evaluated in detail following protein subunit vaccination.

Correspondingly, the prime-boost strategy of Romain, et al. was successful in eliciting an improved immune response following priming with a trivalent DNA vaccine including vectors encoding Apa, Hsp70, and Hsp65 followed by boosting a BCG vaccine. The use of DNA vaccines produces glycosylated antigens (Apa, etc.) as the antigens are expressed in host cells. In the case of Romain, the priming antigens were subjected to mammalian cell glycosylation during expression and any antigenicity or immunogenicity is expected to be the result of glycosylated antigen exposure.

In a preferred embodiment of the instant invention, the polypeptide is produced without glycosylation. In a non-limiting example, polypeptides are synthesized in *E. coli* which is recognized in the art as incapable of properly glycosylating a protein relative to a mammalian cell type or *M. tuberculosis*. It is appreciated the other synthetic means that do not glycosylate the polypeptide are similarly suitable. Thus, in this embodiment protein(s) are free from glycosylation. As the high degree of cellular recognition of Apa, for example, is attributable to the presence of glycosylation, and all prior studies analyzing the immunogenicity or antigenicity of Apa were attributable to glycosylated antigen, it was expected that the absence of glycosylation would not yield efficacious results. Surprisingly in the instant invention, vaccination using non-glycosylated polypeptides resulted in robust immunogenicity.

The instant invention is suitable as a stand alone vaccine, a priming vaccine, or as a boosting vaccine. Preferably, the instant invention is used in a prime-boost strategy. More preferably, the instant invention is used as priming vaccine. When used as priming vaccine the instant invention is illustratively followed by immunization with BCG vaccine or other subunit/DNA vaccine(s). In an embodiment of the invention, a single subunit priming vaccine is employed. Preferably, a vaccine wherein the polypeptide is Apa. It is appreciated that other polypeptides are similarly suitable. In this embodiment immunization with the Apa protein is optionally followed by immunization with a single subunit or multicomponent vaccine illustratively employing more than one protein in addition to or at the exclusion of Apa. Delivery of subsequent vaccinations is optionally within a short or long time period. In a nonlimiting example, the second vaccination is delivered within a single day or week. Alternatively, the second vaccination is delivered after one year or after few years. It is appreciated that a delivery of a second vaccine may be at any time during the subject's lifetime.

Preferably, the second vaccine is protein subunit vaccine or even BCG vaccine (normal or recombinant). Delivery of a second or subsequent vaccine is optionally by the same delivery route as the first immunization or by an alternative route. In a preferred example, a prime vaccine is delivered by the intranasal route. A subsequent boost vaccine is also delivered by the intranasal route.

In a preferred embodiment, delivery of BCG vaccine occurs prior to boosting with a single or multicomponent vaccine. Preferably, BCG vaccination is boosted by delivery of a multicomponent vaccine. More preferably, BCG is boosted by vaccination with a single component vaccine wherein the single component is a polypeptide encoding Apa protein. It is similarly appreciated that delivery of the boost vaccine is optionally delivered at any time during the subject's lifetime.

The instant invention is optionally used as a combination vaccine. Illustratively, a BCG vaccine is supplemented with a single or multicomponent vaccine. This strategy allows for simultaneous delivery of a single polypeptide, multicomponent, and a BCG vaccine in any combination.

In a preferred embodiment, a single or multicomponent vaccine comprising a single or multiple polypeptides is delivered by the intranasal route and a BCG vaccine is delivered by an intradermal or subcutaneous route. More preferably, a single or multicomponent vaccine is delivered by an intranasal route and a boost BCG vaccine is delivered also by an intranasal route. Alternatively, BCG vaccine is given by intranasal or percutaneous route and a boost single or multicomponant vaccine is also delivered by the same route. It is appreciated that methods of delivery known in the art are suitable for delivering vaccine by these or other routes of entry.

Delivery of the inventive vaccine is optionally administered prior to, during, or following active or inactive infection with TB or after development of disease alone or in conjunction with antitubercular chemotherapy. Thus, delivery of a single or multicomponent vaccine is optionally prophylactic, postinfection or therapeutic. In a preferred embodiment, the instant invention is designed to prevent or eliminate disease, or to prevent infection. Optionally, delivery of a single or multicomponent vaccine is therapeutic.

The polypeptide is optionally delivered as naked polypeptide, in aqueous solution, in an emulsion, or in other suitable delivery compositions. In a preferred embodiment the instant invention is delivered as a vaccine or as a vaccine component of a pharmaceutical package. Optionally, a polypeptide (or multiple polypeptides) or immunogenic peptides or epitopes are present in an emulsion comprised of suitable emulsification agents. In a preferred embodiment a multicomponent vaccine is emulsified or encapsulated in a suitable vaccine carrier. More preferably, a single subunit vaccine is emulsified. Most preferably, a polypeptide encoding Apa is emulsified. Suitable emulsification agents illustratively include supramolecular biovectors (SMBV), nanoparticles such as described by Major, M, et al., *Biochim. Biophys. Acta*, 1997; 1327:32-40, De Migel, I, et al., *Pharm. Res.*, 2000; 17:817-824, U.S. Pat. Nos. 6,017,513, 7,097,849, 7,041,705, 6,979, 456, 6,846,917, 6,663,861, 6,544,646, 6,541,030, 6,368,602, Castignolles, N., et al., *Vaccine*, 1996; 14:1353-1360, Prieur, E., et al., *Vaccine*, 1996; 14:511-520, Baudner B, et al., *Infect Immun*, 2002; 70:4785-4790; liposomes such as described by El Guink et al., *Vaccine*, 1989; 7:147-151, and in U.S. Pat. No. 4,196,191; or other agents known in the art. Agents suitable for use are generally available commercially.

Optionally, the instant invention includes codelivery of polypeptides with an adjuvant. Suitable adjuvants illustratively include dimethyl dioctadecyl-ammonium bromide (DDA); monophosphoryl lipid A (MPL); *E. coli* heat-labile enterotoxin, genetically modified derivatives thereof, LTK63, Trehalose Dimycolate and synthetic derivatives, lipophilic quaternary ammonium salt-DDA, DDA-MPL, DDA-TDM, DDA-TDB, IC-31, aluminum salts, aluminum hydroxyide, aluminum phosphate, potassium aluminum phosphate, those described in U.S. Patent Publication 20070212329, antigen-sparing adjuvants, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles illustratively including calcium phosphate nanoparticles, combination of soybean oil, emulsifying agents, and ethanol to form a nanoemulsion; AS04 produced by Glaxo-Smith Kline (Middlesex, UK); ZADAXIN available from SciClone Pharmaceuticals (Hong Kong); other agents known in the art, combinations thereof, or fragments thereof.

The present invention is further illustrated with respect to the following non-limiting examples.

Example 1

BCG, single, and multicomponent vaccine production: The BCG (Copenhagen) vaccine was provided as a TB pre-clinical vaccine reference standard by the Center for Biologics Evaluation and Research, Food and Drug Administration (FDA), Bethesda, USA. Lyophilized BCG vaccine was resuspended in vaccine diluent (diluted Sauton medium; Statens Serum Institute, Copenhagen, Denmark).

For single or multicomponent vaccine production a single dose consisted of 10 μg of each polypeptide emulsified in DDA (250 μg/dose, Sigma-Aldrich, St. Louis, Mo.) and MPL (derived from *Salmonella minnesota* Re 595; 25 μg/dose, Sigma-Aldrich, St. Louis, Mo.). The emulsion was prepared as described by Sable S B et al. Vaccine, 2005; 23: 4175-4184. Briefly, MPL was first mixed with endotoxin-free sterile water (Burdick & Jackson, Muskegon, Mich.) containing 0.2% triethylamine (Fisher Scientific, Fair Lawn, N.J.). The mixture was subjected to three rounds of heating in a 70° C. water bath for 30 s and then sonication for 30 s. An emulsion was prepared by suspending DDA in sterile water and a homogeneous dispersion of the powder was obtained by heating the suspension at 80° C. for 5-10 min in water bath. After cooling to room temperature, MPL and antigens were mixed with DDA just before use.

Example 2

Polypeptide Production: Nine recombinant *M. tuberculosis* H37Rv proteins (Table 1), whole cell lysate (WCL), and total short term culture filtrate proteins (STCF) were obtained through the TB Vaccine Testing and Research Material contract funded by National Institute of Health (NIH)/National Institute of Allergy and Infectious Diseases (NIAID) at Department of Microbiology, Immunology and Pathology, Colorado State University, Fort Collins, Colo.

TABLE 1

| Vaccine candidate | Sanger annotation | Calculated molecular wt (kDa)[a] | Observed molecular wt (kDa)[b] | Lot number | Endotoxin Level (ng/mg)[d] | Function |
|---|---|---|---|---|---|---|
| Ag85A | Rv3804c | 35.55 | 30.5 | 05.rEC.04.28.Ag85A | 1.37 | Mycolyl Transferase/ Fibronectin binding |
| Ag85B | Rv1886c | 34.45 | 29.5 | 05.rEC.04.25.Ag85B | 1.43 | Mycolyl Transferase/ Fibronectin binding |
| MPT-64 | Rv1980c | 24.72 | 24.0 | 05.rEC.05.25.MPT64 | 1.23 | Unknown |

TABLE 1-continued

| Vaccine candidate | Sanger annotation | Calculated molecular wt (kDa)[a] | Observed molecular wt (kDa)[b] | Lot number | Endotoxin Level (ng/mg)[d] | Function |
|---|---|---|---|---|---|---|
| Pst-S1 | Rv0934 | 38.11 | 38.0 | 05.rEC.07.12.Psts1 | 1.90 | Phosphate transporter |
| Apa | Rv1860 | 32.59 | 45-47 | 05.rEC.06.03.ModD | 1.77 | Fibronectin binding/host cell attachment |
| GroES | Rv3418c | 10.67 | 10.0-12.0 | 02.rEC.06.12.GroES | 0.69 | Chaperonin(HSP10)/ATPase |
| GroEL | Rv0440 | 56.70 | 65.0 | 05.rEC.06.08.GroEL2 | 2.09 | Chaperonin (HSP65) |
| Dnak | Rv0350 | 66.70 | 70.0 | 03.rEC.07.21.Dnak | 0.86 | Chaperonin(HSP70)/ATPase |
| CFP-10 | Rv3874 | 10.66 | 10.0 | 05.rEC.07.12.CFP10 | 1.67 | Unknown/ESAT-6 family member |

Alternatively, specific polypeptides were cloned, expressed and isolated. Illustratively, isolation and characterization was performed as described by Sable, S., et al., *Infection and immunity*, 2005; 73:3547-3558 and Sable, S, et al., *Vaccine*, 2005; 23:4175-4184. Briefly, primers used for cloning and sequencing were synthesized at the Biotechnology Core Facility, Centers for Disease Control and Prevention. The following PCR primers for Rv0164 (mtsp-17/TB18.5), Rv0831c (cfp-31) and Rv1324 (cfp-32) gene sequences found in the NCBI database were designed to specifically amplify the corresponding gene and to introduce a BamH1/Nde1 restriction enzyme recognition site: Rv0164 forward, GCT CAT ATG ATG ACG GCA ATC TCG TGC TC (SEQ ID NO 1); Rv0164 reverse, GCT GGA TCC TTA GCT GGC CGC CAG CTG CTC GGC GC (SEQ ID NO 2); Rv0831c forward, GCT CAT ATG CTC CCC GAG ACA AAT CAG G (SEQ ID NO 3); and Rv0831c reverse, GCT GGA TCC TTA CTG GCG AAG CAG CTC AT (SEQ ID NO 4); Rv1324 forward, GCT CAT ATG ACG CGT CCG CGA CCC CCG C (SEQ ID NO 5); and Rv1324 reverse, GCT GGA TCC TCA GTA CAG CGC GTT GGC GAG ((SEQ ID NO 6). DNA fragments were obtained by PCR amplification of *M. tuberculosis* H37Rv chromosomal DNA with these primer sets, purified on agarose gels, and cloned into TOPO TA cloning vector (Invitrogen, CA, USA). Putative recombinant *E. coli* (TOP 10) colonies were selected on Luria-Bertani medium with kanamycin (25 µg/ml). Plasmids were extracted and inserts were confirmed by PCR, restriction enzyme digestion and sequencing. BamH1/Nde1 cleaved inserts were cloned in frame into the expression vector pET19-b (Novagen, CA, USA) and the resulting plasmids were confirmed by sequencing.

The pET19-b expression vector containing the gene of interest was subsequently used to transform *E. coli* BL-21 (DE3) cells (Novagen; EMD Biosciences, CA, USA). The gene encoding the respective recombinant protein was induced in Luria-Bertani medium containing 100 µg/ml ampicillin with 0.25 mM IPTG (isopropyl β-D-thiogalactoside) while incubating 16 h in a 25° C. water bath. The cells were lysed using the Bugbuster kit (Novagen, CA, USA) as per the manufactures instructions, and the recombinant protein was purified from the inclusion bodies using the nickel-nitrilotriacetic acid (Ni-NTA) agarose matrix (His•Bind purification kit; Novagen, CA, USA) after solubilization in the presence of 8 M urea, or from the soluble periplasmic fraction as per the manufacturers protocol. Endotoxin was removed from the columns prior to elution using 0.5% ASB-14 in wash buffer, while on-column refolding was performed as described by Oganesyan, N, et al., 2005; 1345-711X. The recombinant protein preparations were pooled and dialyzed against 0.1 M PBS (pH 7.2). The dialyzed Rv0164 and Rv0831c were further purified by fast protein liquid chromatography using an analytical superdex-200 column (10/300; Amersham Pharmacia Biotech) equilibrated with the same buffer. Rv1324 was purified using UNO Q1 anion-exchange column (Bio-Rad, CA, USA) after dialyzing against 20 mM Tris-HCl (pH 8.2) and using 0-1 M NaCl linear gradient. Fractions were analyzed by SDS-PAGE, buffer exchanged with PBS (pH 7.2) and concentrated on Centricon YM-3 (Millipore, Mass., USA). The purified recombinant proteins were filter (0.22 µM; Millipore, Mass., USA) sterilized and quantified using microBCA protein estimation method (QuantiPro BCA Assay Kit; Sigma-Aldrich, MO, USA). The protein identity was further confirmed by LC-MS-MS. The lipopolysaccharide (LPS) contents in the protein preparations were determined by the *Limulus* amoebocyte lysate assay (LAL-QCL-1000 Assay Kit; Cambrex, MD, USA) as per the manufactures protocol. The proteins were aliquoted and stored at −70° C. until further use.

The expression of the recombinant proteins was consistently achieved at yields ranging from 1-2 mg/L for Rv0164, 4-5 mg/L for Rv0831c and 6-8 mg/L for Rv1324 protein as evaluated by micro BCA method. Silver staining of the gel (FIG. 1) performed under reducing conditions (SDS-PAGE; 4-20% gradient) revealed the molecular weight of 20.0 kDa for purified recombinant Rv0164, 33.0 kDa for recombinant Rv0831c and 37.0 kDa for recombinant Rv1324 protein. The identity of purified proteins was further confirmed by LC-MS-MS. Before the proteins were used for immunization of subjects or in in vitro immunological assays, the preparations were analyzed for contamination with endotoxin (LPS). In all the cases, LPS was present in amounts that are not suspected to interfere with in vivo or in vitro immunogenicity experiments (9.0 EU of LPS/mg of Rv0164, 16 EU of LPS/mg of Rv0831c and Rv1324).

Example 3

Vaccination of Subjects: For mouse subjects, BCG vaccine was delivered by subcutaneous vaccination by administration of 50 µl of a BCG suspension ($7\times10^5$ CFUs) injected above the gluteus superficialis and biceps femoralis muscles of both hind legs using a 26 gauge needle. BCG vaccine was administered by applying a total of 30 µl of BCG vaccine ($7\times10^5$ CFUs) to the external nares (15 µl per nostril) using a fine tip micropipette and allowing the mouse to inhale the suspension into the lungs naturally. For all studies, BCG vaccine diluent was used as a control for either route of vaccination. Vaccination of human subjects is performed similarly. BCG dosing for human subjects is between $1\text{-}8\times10^5$ CFU administered intranasally or by subcutaneous injection.

Multicomponent vaccine was delivered to mice by the intranasal route three times at 2-week intervals as described above except using 90 µg of recombinant *M. tuberculosis* protein mixture per dose (10 µg of each polypeptide). Dosage of human subjects involves the administration of 10-1000 µg of each polypeptide. The dose range for large animal subjects approaches that of humans with similarly sized receiving compartments. Small animals required dosage at the low end of the spectrum as the receiving compartment is proportionally smaller in size. For all studies sham immunization was performed by administration of phosphate buffered saline (PBS) (pH 7.2) DDA-MPL.

Example 4

Sample collection: Collection of blood from small animals was performed by cardiac puncture under anesthesia at targeted time points. Large animals and human subjects were/will be drawn intravenously into suitable anticoagulant. Urine was collected by established procedures. Nasal lavage was performed by repeated flushing of the nares and associated upper respiratory tract of the sacrificed mouse with 200 µl of PBS (pH 7.2) containing complete EDTA-free protease inhibitor cocktail (Roche Diagnostics GmbH, Mannheim, Germany). Serum, urine and nasal washings were stored at −20° C. until use.

For mouse studies, samples from the lungs, spleen, nasal associated lymphoid tissue (NALT), cervical lymph nodes (CLN), inguinal lymph nodes (ILN), mesenteric lymph nodes (MLN) and femur and tibial bone marrow (BM) were aseptically removed and placed into RPMI 1640 supplemented with 100 IU/ml penicillin, 50 µg/ml streptomycin, 1 mM L-glutamine, 25 mM HEPES, 1 mM sodium pyruvate, $5 \times 10^{-5}$ M β-mercaptoethanol, vitamins and nonessential amino acids (Gibco-Invitrogen, Grand Island, N.Y.) and 10% endotoxin-tested heat-inactivated fetal calf serum (FCS; Atlas Biologicals, Fort Collins, Colo.). Thoracic and peritoneal exudates cells were isolated by washing the respective cavities with RPMI 1640 media.

Example 5

Isolation of immune cells: To isolate lung cells, mice were bled by cardiac puncture under anesthesia and their lungs were perfused via the right ventricle with PBS containing 10 U ml$^{-1}$ heparin to remove intravascular leukocytes. The lungs were then perfused with an enzyme mixture containing 1 mg/ml collagenase type IV (Sigma-Aldrich, St. Louis, Mo.) and 25 U ml$^{-1}$ DNase (Roche, Penzberg, Germany) in supplemented RPMI and sliced into small pieces in a sterile dish and the fragments were incubated in the enzyme mixture at 37° C. for 1 h. The digested lung fragments were pressed with a 5 ml syringe plunger through a 70-µm pore size cell strainer (BD Falcon, Bedford, Mass.) to obtain a single cell suspension and erythrocytes were lysed with RBC lysis buffer (eBioscience, San Diego, Calif.) for 4-5 min at room temperature. The lung cells were washed, recovered by centrifugation, and resuspended in supplemented RPMI for counting using the trypan blue dye exclusion method. The NALT was isolated as described (Asanuma, H, et al. *J Immunol Methods,* 1997; 202:123-131), and BM was isolated by flushing cavities of femurs and tibias with RPMI. Single cell suspensions of spleen, lymph nodes, BM or NALT were obtained by gently grinding the respective organs through a 70-µm cell strainer into 10-20 ml supplemented RPMI. Cell suspensions were centrifuged at 300×g for 10 min and the erythrocytes were removed by treatment with RBC lysis buffer when necessary. Cells were washed several times with fresh RPMI and the cell concentration was adjusted accordingly.

Example 6

Th1 responses from intranasal and subcutaneous BCG administration: Following intranasal or subcutaneous administration the frequency and distribution of interferon-γ (IFN-γ), IL-2, and IL-4 secreting antigen-specific T-cells in lungs, spleen and respective draining lymph nodes were measured over the course of 12-weeks. Cells were isolated as described above with the total number of cells obtained independent of the type of immunization performed. *M. tuberculosis* WCL-specific IFN-γ, IL-2 and IL-4 responses were evaluated in the lungs and spleen after both i.n. and s.c BCG immunization (FIG. 1) by IFN-γ, IL-2, and IL-4 ELISPOT assay kits according to the manufacturers protocol. (BD-Biosciences, San Diego, Calif.).

More IFN-γ, IL-2 and IL-4 secreting cells were found in the lung and draining CLN after i.n. immunization than after subcutaneous (s.c.) immunization at all three time points evaluated except more WCL-specific IL-4-secreting SFUs were observed in the lungs after s.c. BCG-immunization than after i.n. immunization at the 12 week time point (p<0.0001). Conversely, s.c. BCG-immunization induced higher WCL-specific IFN-γ, IL-2 and IL-4 responses in the ILN, which drains the flank (the site of vaccination), and spleen as compared to i.n. immunization at all time points evaluated except for IFN-γ and IL-2, where more WCL-specific SFUs were observed in the spleens of the i.n. group than the s.c. group at the 12 week time point (p<0.01 and 0.05 for IFN-γ and IL-2 respectively).

Example 7

Nitric Oxide production following BCG immunization alone: Nitrite ($NO_2^-$) accumulation in the supernatant of cultured cells was measured as an indicator of nitric oxide (NO) production by a Griess assay using a sodium nitrite standard as described by Sable, S, et al., *Eur Respir J,* 2007; 29:337-346. Supernatants (100 µl) from $1 \times 10^6$ cells ml$^{-1}$ of each condition stimulated with 10 µg ml$^{-1}$ WCL, *E. coli* LPS-TLR-4 ligand (InvivoGen, San Diego, Calif.) or RPMI medium alone after 96 h of culture at 37° C. were assayed in triplicate, and the absorbance was measured at 550 nm.

Figure 3:
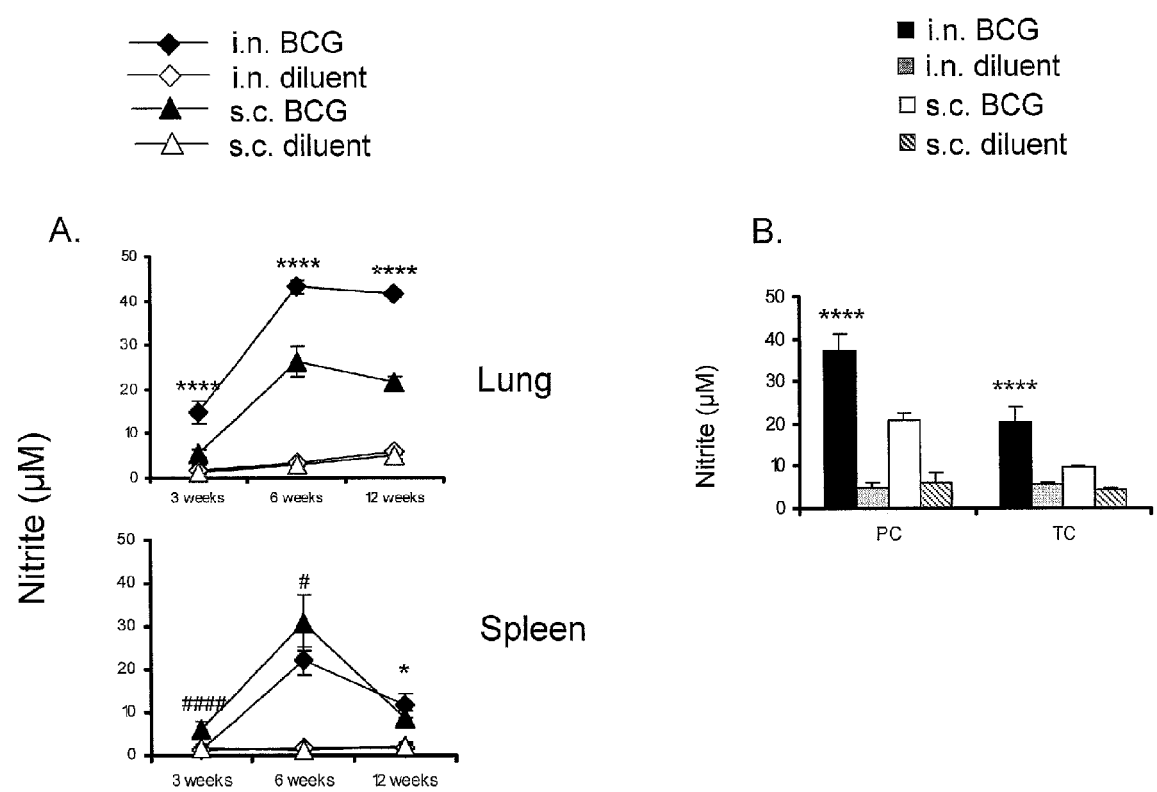
FIG. 3 represents kinetics of NO response induced by intranasal or subcutaneous BCG vaccination.

WCL stimulation of lung cell cultures from mice intranasally immunized with BCG produced significantly higher nitrite levels at all the three time points compared to intranasally diluent immunized (p<0.0001) or subcutaneously BCG immunized mice (p<0.0001) (FIG. 3A). WCL-induced nitrite levels in the spleen cell cultures following subcutaneous BCG immunization were significantly higher than those observed following subcutaneous diluent immunization at all the three time points (p<0.0001) and intranasal BCG immunization at the 3 week (p<0.0001) and 6 week (p<0.05) time points. However, at the 12 week time point intranasal BCG immunization induced increased levels of WCL-specific nitrite levels in the spleen as compared to subcutaneous BCG immunization (p<0.05), although the levels in each case were relatively low (FIG. 3A).

Furthermore, thoracic and peritoneal exudate cells following intranasal BCG immunization were found to produce significantly higher levels of nitrite after stimulation with WCL (p<0.0001) than those isolated following subcutaneous BCG immunization at 12 weeks (FIG. 3B).

The ability of i.n. BCG immunization to induce mycobacterium-specific Th1 (IFN-γ and IL-2) and Th2 (IL-4) cytokine responses in various local and distant immune compartments was evaluated using ELISPOT and lymphocyte proliferation at 6 and 30 weeks post immunization and two *M. tuberculosis* antigen preparations, STCF and WCL.

Cells isolated from different sites were seeded in sterile 96-well flat-bottom tissue culture plates (Costar, Corning, N.Y.) at $1 \times 10^6$ cells/ml in 100 µl of supplemented RPMI- 1640. BM derived dendritic cells (DC) were used at 5:1 lymphocytes/DC. For each treatment group, cells were stimulated in triplicate or quadruplet with either 100 μl of 10 μg/ml purified recombinant *M. tuberculosis* antigen, antigen combination, WCL, STCF, or Con-A in supplemented RPMI as a positive control for cell viability and reactivity or medium alone as a negative control. Cultures were incubated in a humid atmosphere containing 5% $CO_2$ at 37° C. for 72 h. 1 μCi of $^3$H-thymidine (Perkin Elmer, Wellesley, Mass.) was added to each well and after 18-20 h incubation the cells were harvested on glass fiber filters (Perkin Elmer, Wellesley, Mass.) using an automated cell harvester (TOMTEC, Inc. Hamden, Conn.). Once dry, the radioactivity incorporated was counted using a β-scintillation counter (Perkin Elmer, Wellesley, Mass.). The proliferation was expressed as mean counts per minute (CPM) of antigen stimulated cultures after subtracting mean counts per minute of cultures without antigen and the stimulation index (SI) was calculated by dividing mean counts per minute in antigen-stimulated wells by mean counts per minute in unstimulated wells.

Figure 4:
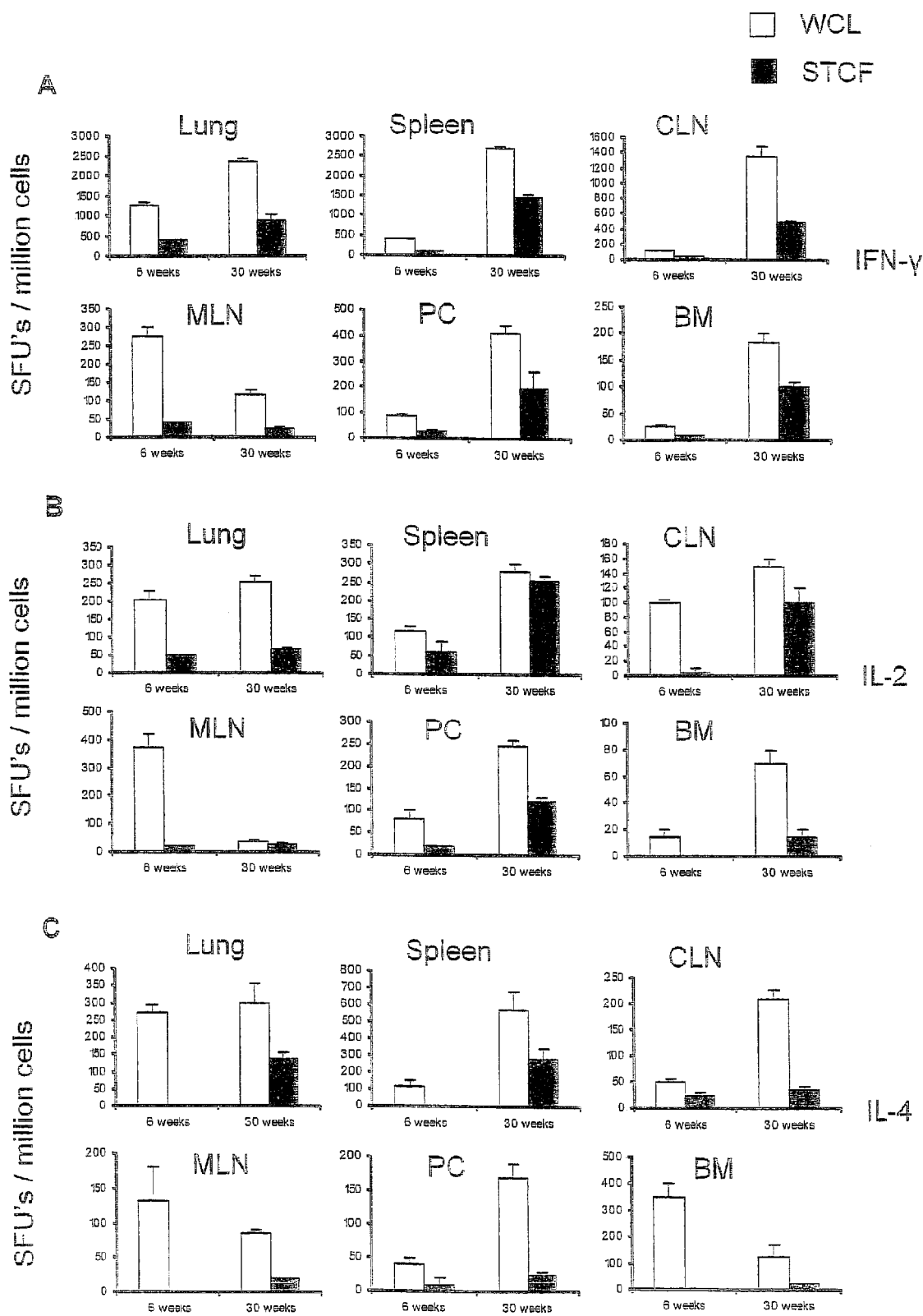
FIG. 4 represents the distribution of *M. tuberculosis* whole cell lysate (WCL) and short term culture filtrate (STCF) specific T-cells in local and peripheral immune compartments of subjects at early (6 weeks) and late (30 weeks) time points after intranasal BCG vaccination wherein the results are presented as means±standard deviation of three to six determinations after subtracting the SFUs from respective unstimulated cultures.

Intranasal BCG immunization induced both STCF- and WCL-specific long-term T-cell responses in the lungs, the local lymph nodes draining the nasal passage (i.e. CLN) and the spleen (FIG. 4). Strong cytokine responses were also observed at 6 weeks post-immunization in the MLN which drains the gastrointestinal tract. However, the STCF- and WCL-specific responses in MLN declined at 30 weeks. Peritoneal exudate cells (PEC) demonstrated an increased response from 6 weeks to 30 weeks of STCF- and WCL-specific Th1 and Th2 cytokines secreting cells following intranasal BCG immunization. Both STCF- and WCL-specific IFN-γ and IL-2 secreting SFUs also increased from 6 weeks to 30 weeks in bone marrow cells while WCL-specific IL-4 SFUs decreased from 6 weeks to 30 weeks. NALT demonstrated both STCF- and WCL-specific proliferation at early (SI 12.15 and 18.60 at 6 weeks respectively; mean CPM of unstimulated culture 720) and late (SI 10.26 and 12.52 at 30 weeks respectively; mean CPM of unstimulated culture 660) time points.

Figure 5:
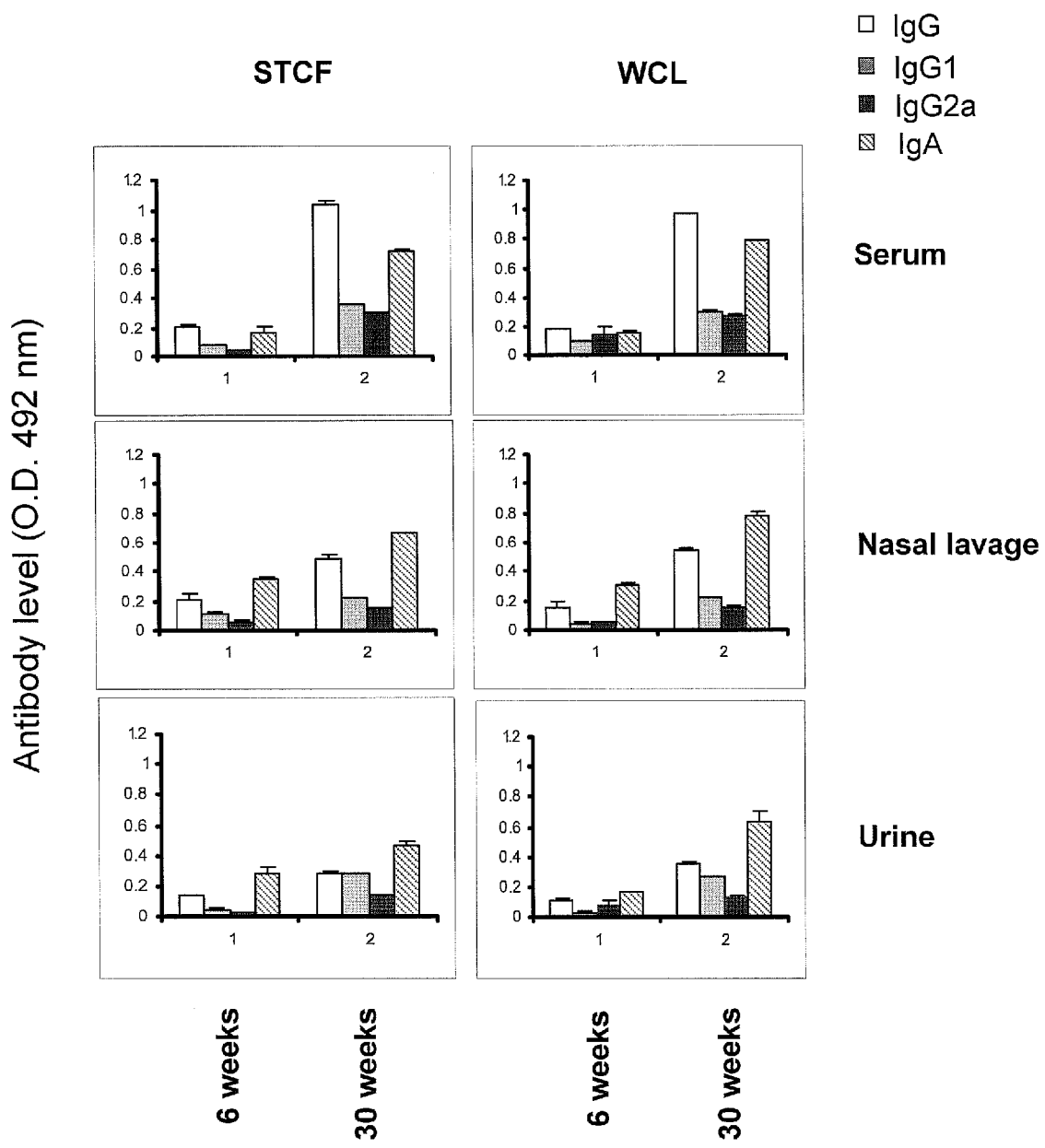
FIG. 5 represents *M. tuberculosis* whole cell lysate (WCL) and short term culture filtrate (STCF) specific antibody levels in local and peripheral body fluids of subjects at early (6 weeks) and late (30 weeks) time points after intranasal BCG vaccination wherein the results of ELISA measurements are presented as mean absorbance of triplicate wells at 492 nm±standard deviation after subtracting the absorbance of control wells.

STCF- and WCL-specific antibody allotype (IgG and IgA) and isotype (IgG1 and IgG2a) levels were evaluated in serum, nasal lavage and urine of intranasal BCG immunized mice. Immunization via the intranasal route induced significantly elevated antigen-specific antibody responses at 30 weeks as compared to the 6 week time point (FIG. 5) and was characterized by predominant antigen-specific IgG allotype levels in serum and IgA levels in nasal lavage and urine.

Example 8

Figure 6:
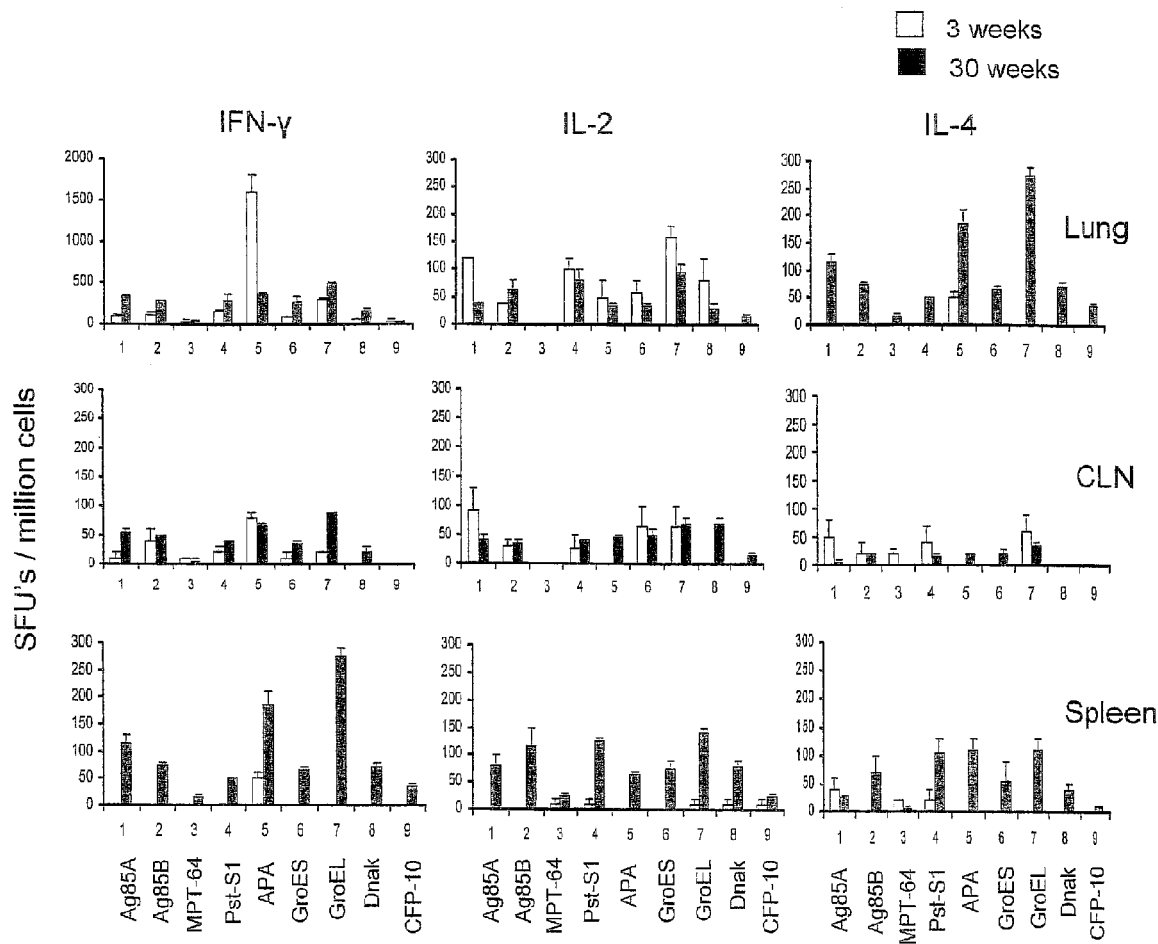
FIG. 6 represents the ability of *M. tuberculosis* recombinant antigens to induce T-cell responses in intranasally BCG-vaccinated subjects at early (3 weeks) and late (30 weeks) time points wherein the results of ELISPOT assays are presented as means±standard deviation of duplicate determinations after subtracting the SFUs from respective unstimulated cultures.

IFN-γ responses induced by polypeptides of *M. tuberculosis* following intranasal BCG immunization: The ability of *M. tuberculosis* polypeptides to be recognized by T- and B-lymphocytes at 3 and 30 weeks was evaluated and is illustrated in FIG. 6.

Recognition of all antigens was higher in the lungs and CLN at the 3 week time point than in cells from the spleen. Among all antigens evaluated, Apa induced the strongest IFN-γ response at 3 weeks, while GroEL induced the strongest IFN-γ response at 30 weeks. In general, the IFN-γ responses induced by Ag85A, Ag85B, Pst-S1 and GroES were moderate compared to those induced by Apa or GroEL. The Apa-induced IL-2 response was low as compared to the GroEL-induced response at all time points evaluated. The pattern of antigen recognition evaluated at 30 weeks in MLN, PEC and BM was similar to that observed in lung, CLN and spleen (FIG. 5), although the magnitude of antigen-specific responses varied from organ to organ.

Antigen-specific allotype and isotype responses in serum, nasal lavage and urine were low at 3 weeks. However, at 30 weeks the strongest antibody response observed was against Ag85 complex proteins (mean serum IgG $A_{492}$ 1.189±0.009 for Ag85B) followed by Pst-S1, while Apa-specific antibody responses were moderate (mean $A_{492}$ range 0.3-0.1) as compared to rest of the antigens (mean $A_{492}$<0.1).

Example 9

Figure 7:
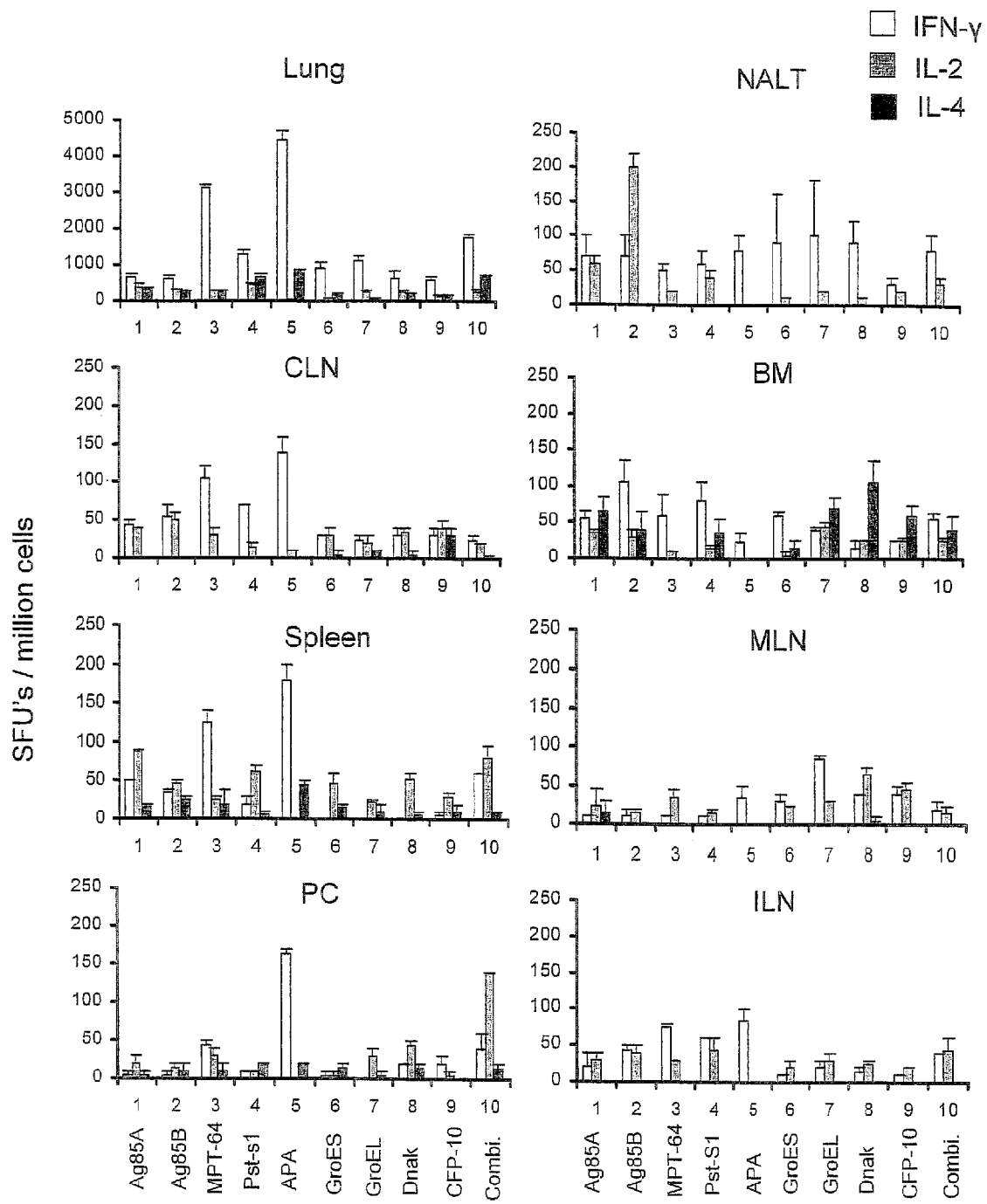
FIG. 7 represents the ability of *M. tuberculosis* recombinant antigens to induce T-cell response in subjects immunized intranasally with the multicomponent subunit vaccine 2 weeks post immunization wherein the results of ELISPOT assays are presented as means±standard deviation of duplicate determinations after subtracting the SFUs from respective unstimulated cultures.

T-cell and antibody responses following multicomponent polypeptide vaccination: The frequency of Th1 and Th2 cytokine secreting cells in different immune compartments after in vitro stimulation with individual polypeptides is illustrated in FIG. 7. Following intranasal immunization with polypeptide multicomponent cocktail-DDA-MPL, all nine polypeptides were more strongly recognized by lung T-lymphocytes than those derived from other organs as evaluated by ELISPOT (FIG. 7) and T-cell proliferation ($^3$H thymidine uptake) assay. The order of recognition of individual polypeptides in terms of induction of IFN-γ secreting cells at the level of the lungs was Apa>MPT-64>Dnak>Pst-S1>GroEL>GroES>Ag85A>Ag85B>CFP-10. The antigen recognition pattern was similar in all immune compartments evaluated with the exception of NALT, MLN, and BM. Although Apa induced both IFN-γ and IL-4 producing cells at the majority of sites following immunization, the frequency of IL-2 secreting cells was low. On the other hand, Ag85 complex (A and B), Pst-S1 and Dnak were observed to be prominent inducers of IL-2 secreting cells.

The results of multiplexed microsphere-based cytokine immunoassays to measure cytokine induction by individual polypeptides demonstrated that elevated levels of IL-12(p70), TNF-α, GM-CSF, IL-4 and IL-10 were secreted in lung cell culture supernatants in response to Apa stimulation. Among the purified antigens evaluated Ag85A, Ag85B and Pst-S1 induced the strongest IL-2 response while IL-2 levels produced by Apa were lowest (Table 2).

The ability of individual polypeptides to induce cytotoxic T-cell responses following multicomponent-subunit immunization was evaluated. Only Apa induced significant macrophage cytotoxicity (mean percentage cytotoxicity 30%) as observed by reduced neutral red uptake by target cells (data not shown).

TABLE 2

| Cytokine Released | Protein (s) used for in vitro stimulation | | | | | | | | | | | | |
|---|---|---|---|---|---|---|---|---|---|---|---|---|---|
| (pg/ml)$^2$ | No Ag | Ag85A | Ag85B | MPT-64 | Pst-S1 | Apa | GroES | GroEL | Dnak | CFP-10 | Cocktail | STCF | WCL |
| IL-2 | 18.4 | 859.3 | 863.4 | 424.1 | 739.9 | 176.6 | 525.4 | 393.5 | 659.9 | 367.6 | 700.0 | 609.0 | 778.0 |
| IL-12 (p70) | BDL | 4.2 | 8.3 | 24.8 | 1.0 | 24.0 | BDL | 8.3 | 4.2 | BDL | 16.2 | 20.1 | 33.7 |
| TNF-α | 4.1 | 23.2 | 32.7 | 47.0 | 32.7 | 47.5 | 27.9 | 43.2 | 23.2 | 13.7 | 56.5 | 58.9 | 358.6 |

TABLE 2-continued

| Cytokine Released (pg/ml)[2] | No Ag | Ag85A | Ag85B | MPT-64 | Pst-S1 | Apa | GroES | GroEL | Dnak | CFP-10 | Cocktail | STCF | WCL |
|---|---|---|---|---|---|---|---|---|---|---|---|---|---|
| GMCSF | 75.0 | 130.1 | 161.3 | 162.5 | 111.9 | 203.9 | 136.4 | 106.9 | 157.5 | 96.3 | 594.7 | 467.3 | 753.6 |
| IL-4 | 2.9 | 33.3 | 24.9 | 42.1 | 20.3 | 67.9 | 13.8 | 16.2 | 14. | 15.7 | 54.0 | 35.0 | 44.0 |
| IL-5 | 193.7 | 267.1 | 352.9 | 266.7 | 118.6 | 203.6 | 212.8 | 148.4 | 382.1 | 209.1 | 745.4 | 579.7 | 876.5 |
| IL-10 | 43.9 | 51.3 | 65.8 | 55.0 | 43.9 | 102.9 | 51.3 | 51.3 | 62.2 | 43.9 | 131.5 | 156.0 | 399.1 |

Protein (s) used for in vitro stimulation

Example 10

Figure 8:
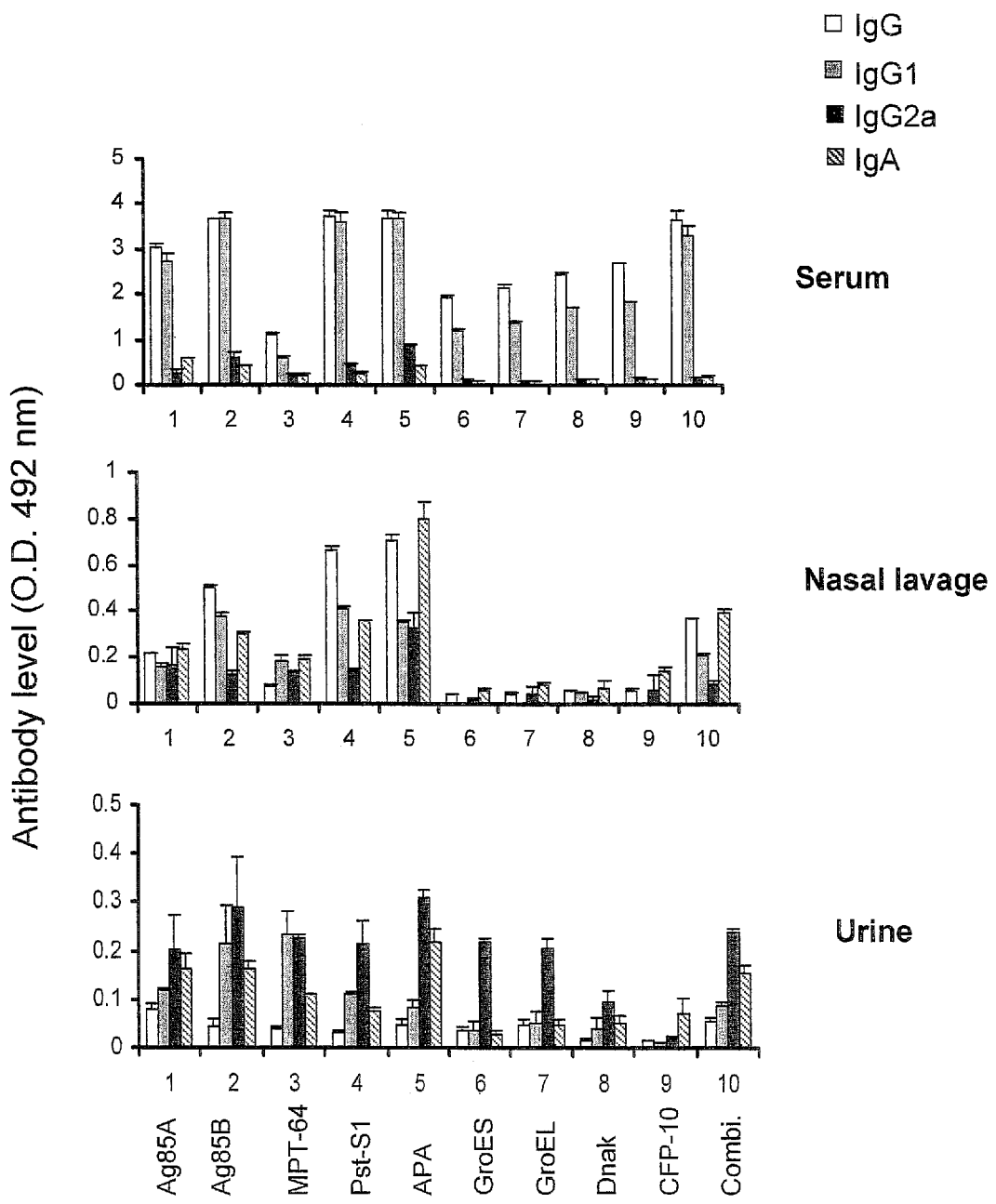
FIG. 8 represents *M. tuberculosis* recombinant antigen-specific antibody response in subjects immunized intranasally with the multicomponent subunit vaccine 2 weeks post immunization wherein results are presented as mean absorbance at 492 nm±standard deviation from triplicate determination after subtracting the absorbance of control wells.

Polypeptide specific antibody responses following intranasal multicomponent immunization: Intranasal immunization induced predominantly immunogen-specific IgG levels in serum while both IgA and IgG levels were observed in the nasal lavage (FIG. 8). Apa induced prominent IgA, IgG1 and IgG2a isotype responses in nasal lavage, serum, and urine respectively. Pst-S1, Ag85B and Ag85A also induced strong humoral responses.

Example 11

Inhibition of *M. tuberculosis* bacilli in infected macrophages by Apa expanded lymphocytes following BCG immunization: The in vitro effect of antigen-expanded effector T-lymphocytes on intracellular *M. tuberculosis* growth in macrophages was carried out as described by Worku and Hoft, *Infect Immun*, 2003; 71:1763-1773 with the following modifications. Peritoneal macrophages from BCG-immunized or sham-immunized mice were prepared by culturing the peritoneal exudate cells in 24-well plates (Costar, Cambridge, Mass.) and macrophages allowed to differentiate for 5 days in the presence of peritoneal T-cells at 37° C. After 5 days nonadherent cells were removed by gentle washing to obtain adherent macrophage population. Effector cells, lung cells and splenocytes ($2\times10^5$ cells/ml) from BCG-immunized or sham-immunized mice were cultured for 5 days in RPMI medium alone to serve as rested T-cell negative controls or stimulated for 5 days with WCL (20 µg/ml) or Apa (10 µg/ml) in 24-well plates. On day 6, macrophages were infected with *M. tuberculosis* at a multiplicity of infection of 1. After 4 hr, the extracellular bacilli were removed by centrifugation at low speed (<1,000 rpm) and the macrophages resuspended in fresh medium. Infected macrophages were seeded at $1\times10^6$ cells $ml^{-1}$ in 96-well plates (100 µl $well^{-1}$) and co-cultured with nonadherent lung or splenic effector cells (100 µl $well^{-1}$) at a 1:1 ratio for 72 hr at 37° C. with 5% $CO_2$ The enumeration of CFU at 72 hr was performed by lysing the macrophages with 0.06% sodium dodecyl sulfate (Sigma-Aldrich, St. Louis, Mo.) for 15 min. Three sets of serial 10-fold dilutions of the lysates from each well were prepared in 0.05% Tween-80 (Sigma-Aldrich, St. Louis, Mo.) and plated on 7H11 agar. Colonies were counted after 3-4 weeks of incubation at 37° C. with 5% $CO_2$ Percentages of *M. tuberculosis* growth inhibition were determined by using the following formula: percent inhibition=100−[100×[(CFU from antigen stimulated T-cells)/(CFU from medium-rested T-cells)]].

Figure 9:
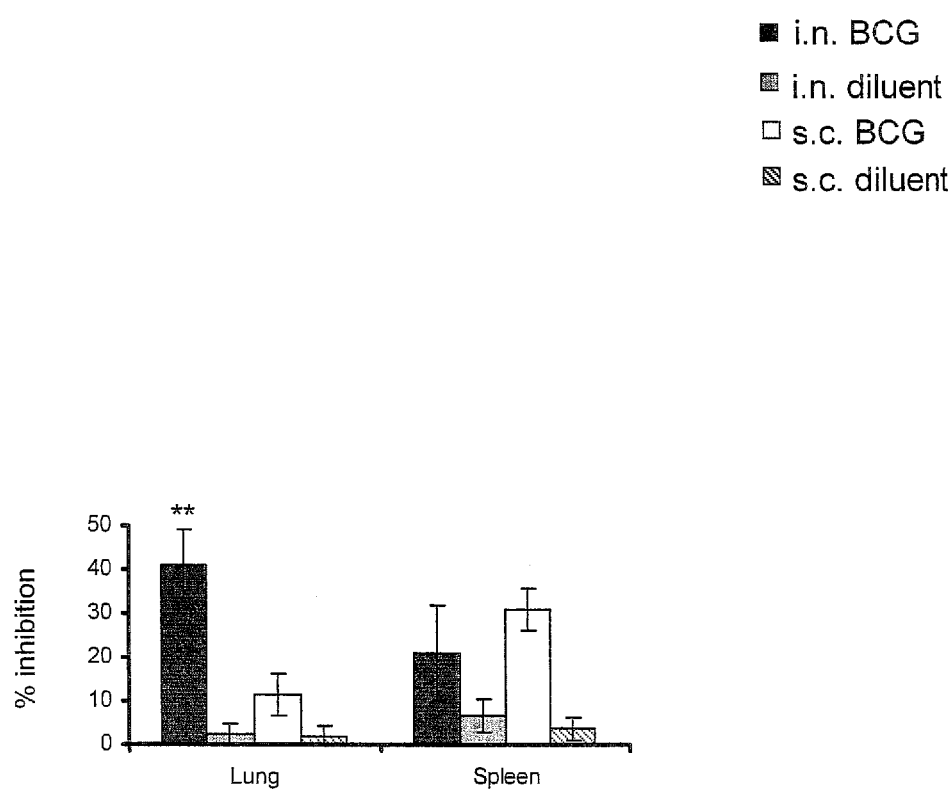
FIG. 9 represents T-cells expanded with Apa inhibiting intracellular growth of *M. tuberculosis* in macrophages at 6 weeks post-immunization.

Lung T-cells isolated 6 weeks after intranasal BCG immunization and expanded with Apa exhibited greater inhibition of the growth of *M. tuberculosis* in peritoneal macrophages compared to medium-only expanded T-cells. (FIG. 9) Further, inhibition was significantly higher than that imparted by lung cells isolated following subcutaneous BCG immunization ($p<0.01$).

Example 12

Figure 10:
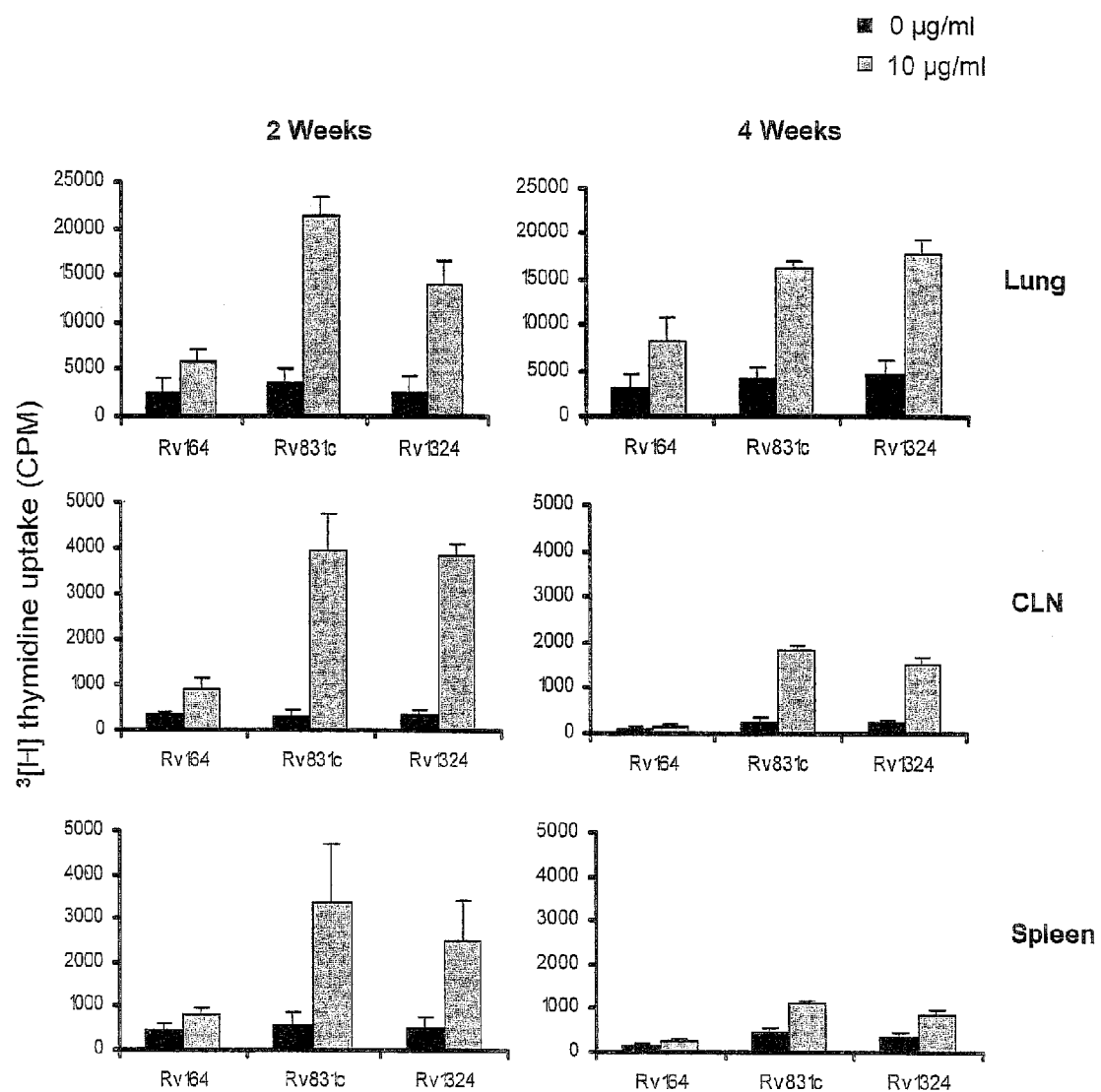
FIG. 10 represents polypeptide immunogen specific proliferative responses in intranasally immunized subjects wherein Rv0164, Rv0831c, and Rv1324 are individually encapsulated in cationic liposome and individually administered.
Figure 11:
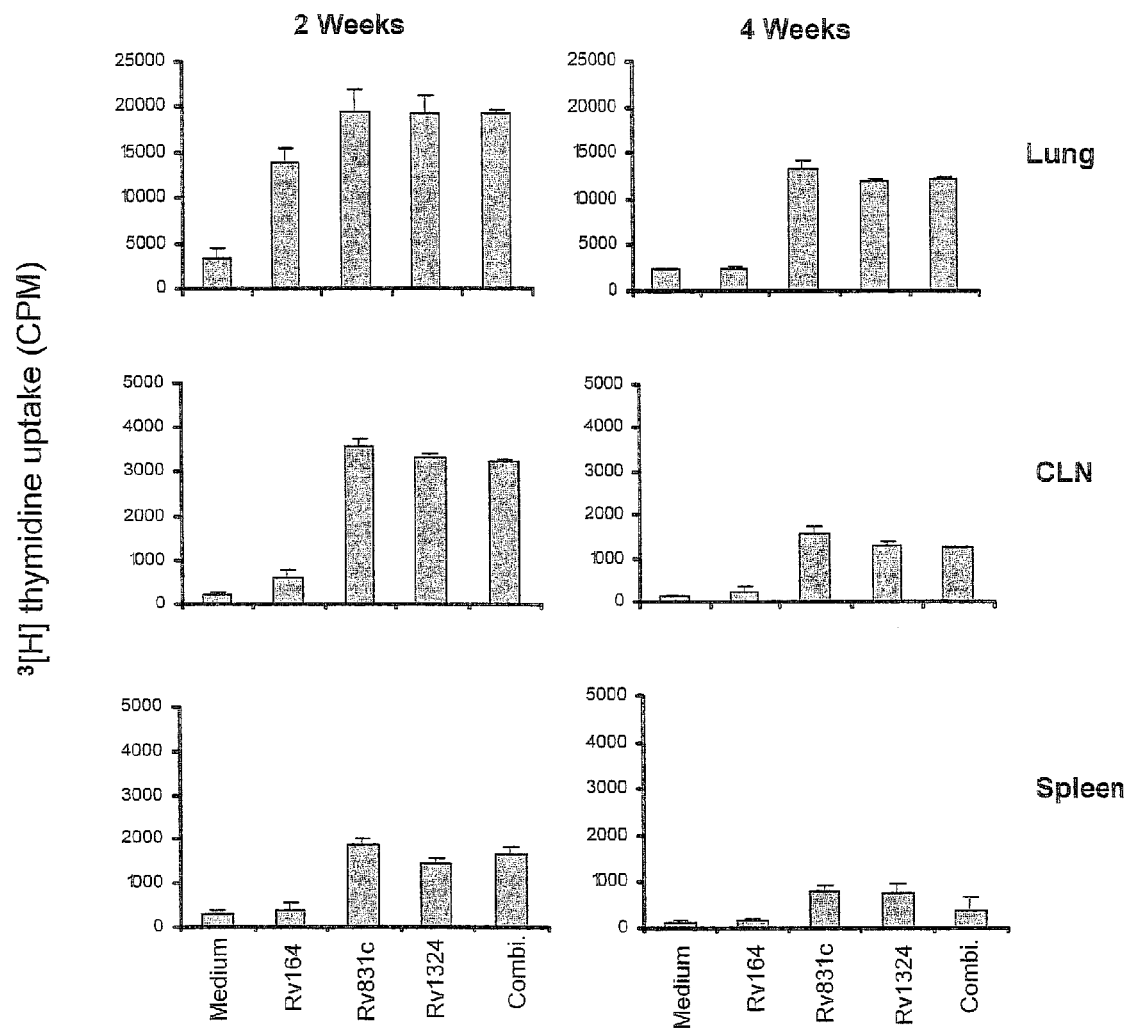
FIG. 11 represents polypeptide immunogen specific proliferative responses in intranasally immunized subjects with the combination of Rv0164, Rv0831c, and Rv1324 encapsulated in cationic liposome.

Induction of proliferative responses following intranasal immunization with single component vaccine: The ability of individual polypeptides to induce proliferative responses in cells isolated from lungs, CLN, or spleen was evaluated following intranasal immunization with a single or multiple polypeptide vaccine comprising polypeptide encapsulated with cationic liposomes. $^3[H]$ thymidine incorporation was evaluated as a measurement of proliferative response. Lung cells demonstrated higher incorporation than cells isolated from spleen following in vitro stimulation with representative polypeptides. (FIG. 10) The polypeptides Rv0831c and Rv1324 induced comparable proliferative response in different target organs while the response induced by Rv0164 was low as evaluated at 2 and 4 week time points. Immunization with polypeptide encoding Apa also induces a strong proliferative response following intranasal immunization that is observed both at 2 week post immunization Following immunization with a combination of Rv0831c, Rv1324, and Rv0164 (10 µg of each protein/dose), Rv0831c and Rv1324 induced significantly better proliferation in target organ cultures after in vitro stimulation as compared to Rv0164 (FIG. 11).

Example 13

Figure 12:
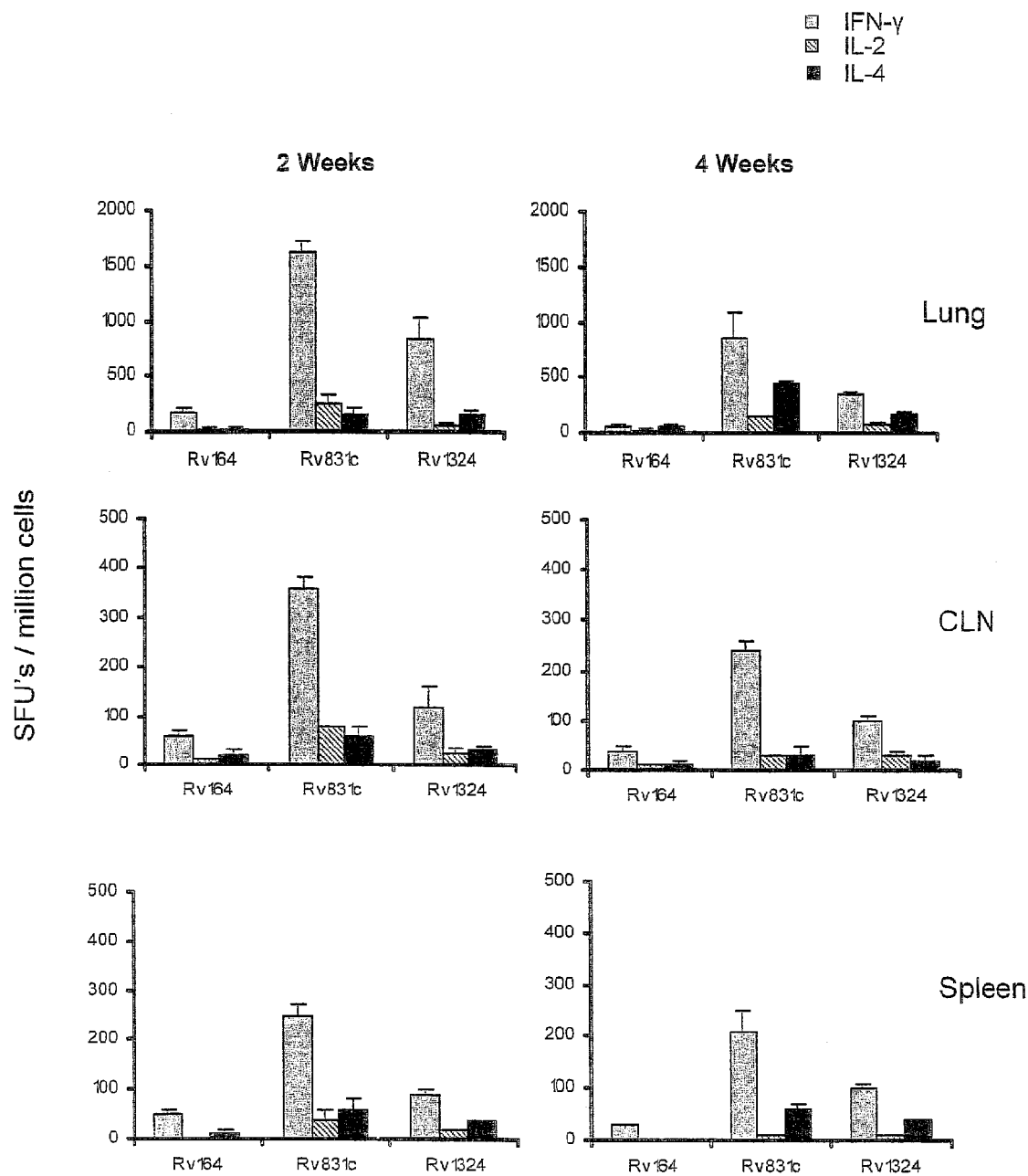
FIG. 12 represents the distribution of polypeptide immunogen specific T-cells in lungs, CLN, and spleen of subjects intranasally immunized with a single polypeptide encoding either Rv0164, Rv0831c, or Rv1324.

Frequency of immunogen specific cytokine secreting cells following single or multicomponent intranasal immunization: The ability of Rv0831c, Rv1324, or Rv0164 to induce Th1 and Th2 cytokine secreting cells was evaluated by ELISPOT as described in the previous example. Intranasal immunization with Rv0831c demonstrated a higher number of IFN-γ, IL-2 and IL-4 secreting cells compared to immunization with Rv1324 or Rv0164 at 2 and 4 weeks post immunization. (FIG. 12) Immunization with Apa produces high levels of Th1 and Th2 cytokine secreting cells. The frequency of individual immunogen specific cytokine secreting cells was higher at the level of lungs among the three organs evaluated, comparable to the results of proliferation assays.

When three polypeptides were intranasally coadministered, Rv0831c induced higher numbers of cytokine secreting cells than Rv1324 and Rv0164. The levels observed in the lungs for Apa protein was more than two-fold higher than Rv0831c (compare FIGS. 7 and 12).

Example 14

Immunogen specific allotype and isotype response in serum and nasal lavage following single or multicomponent intranasal immunization: The allotype and isotype immunoglobulin response was measured 2 and 4 weeks post immunization by ELISA. Briefly, total immunoglobulin G (IgG), immunoglobulin A (IgA), and IgG isotypes IgG1 and IgG2a specific to purified recombinant antigens and antigen combination were estimated. Individual antigens or antigen mixture suspended at a concentration of 2 µg/ml in 100 µl of coating buffer (0.05 M Carbonate, pH 9.5) were allowed to bind to wells of MaxiSorp ELISA plates (Nalge Nunc International, Rochester, N.Y.) for 2 h at 37° C. After three washes with PBS-T, the wells were blocked overnight at 4° C. with 3% bovine serum albumin (BSA, Sigma-Aldrich, St. Louis, Mo.) in PBS-T. Serum or nasal lavage samples (100 µl) were added per well at a 1:200 or 1:100 dilutions respectively in PBS-T containing 1% BSA. Antigen antibody binding was allowed to proceed for 2 h at 37° C. The plates were washed four times with PBS-T, and 100 µl of horseradish peroxidase-conjugated anti-mouse secondary antibodies (anti-mouse IgG and IgA, Sigma-Aldrich, St. Louis, Mo. and anti-mouse IgG1 and IgG2a, BD-Biosciences, San Diego, Calif.) diluted 1:1,000 in PBS-T containing 1% BSA were added to respective wells. After 90 min the plates were washed six times with PBS-T. The reaction was developed with o-phenylenediamine (Sigma-Aldrich, St. Louis, Mo.) and hydrogen peroxide in citrate substrate buffer (pH 5.0). The reaction was stopped after 20 min by adding 100 µl of 1 M $H_2SO_4$ and the absorbance was measured at 492 nm ($A_{492}$).

Figure 13:
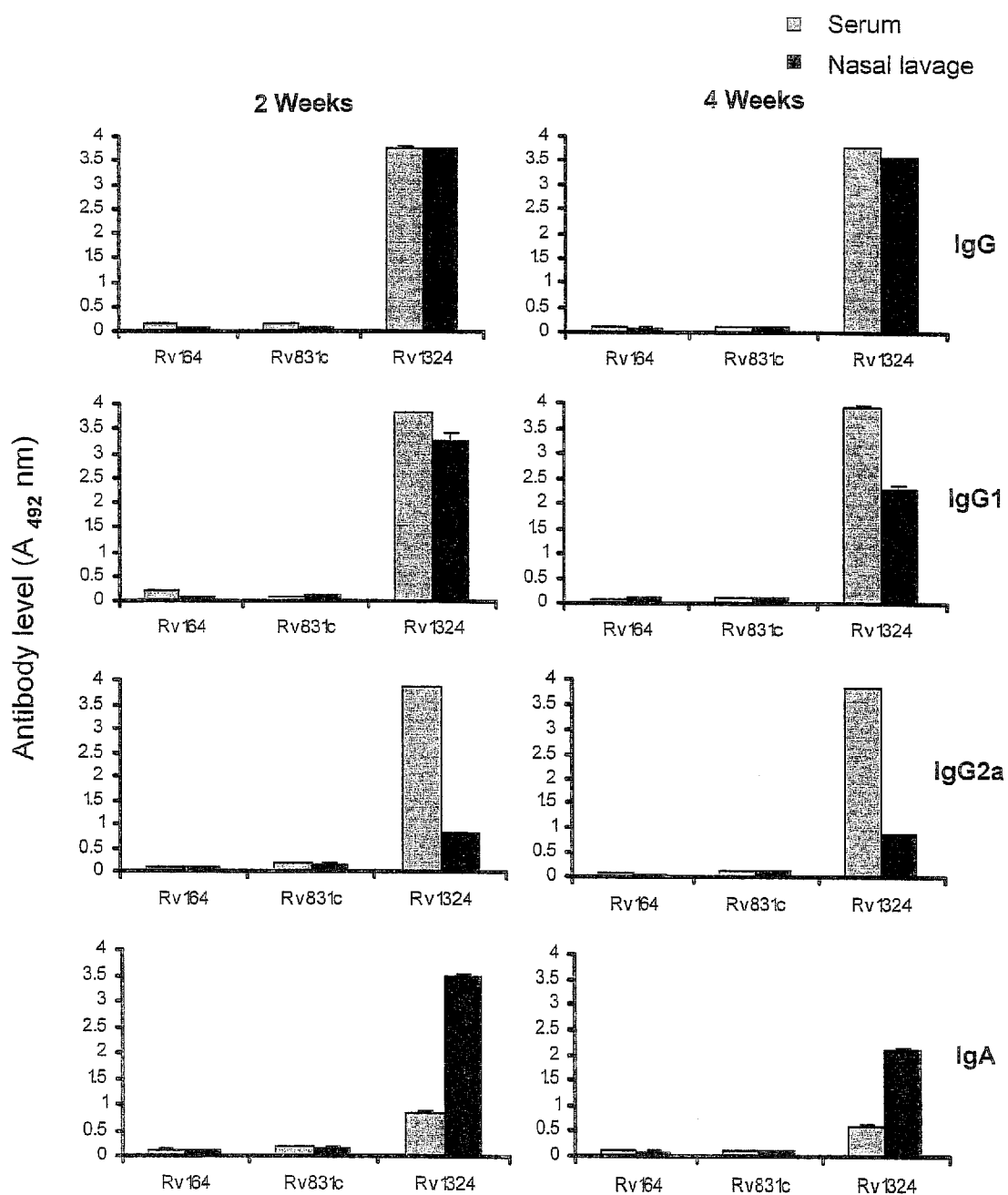
FIG. 13 represents polypeptide immunogen specific allotype and isotype antibody responses in the nasal lavage and serum from subjects immunized with cationic liposome encapsulated recombinant Rv0164, Rv0831c, or Rv1324 at 2 and 4 weeks post immunization.

Immunization with Rv1324 demonstrated a strong immunogen specific antibody response in excess of that observed for Rv0831c and Rv0164. (FIG. 13) Intranasal Rv1324 immunization induced antibody response was characterized by strong immunogen specific IgG response with both IgG1 and IgG2a isotype levels in the serum and mixed IgA and IgG response with predominant IgG1 isotype levels in the nasal lavage as evaluated at both 2 and 4 week time points.

Figure 14:
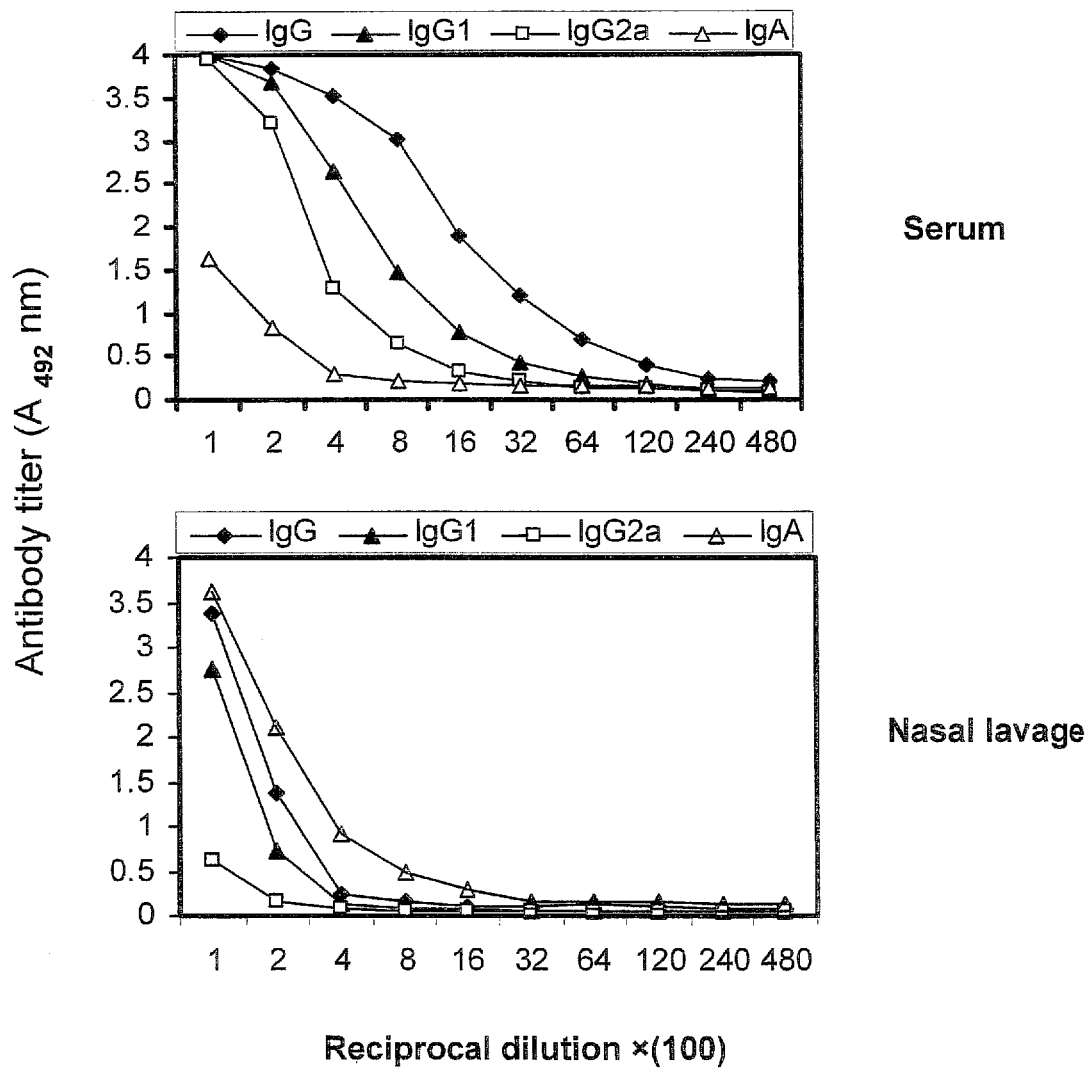
FIG. 14 represents polypeptide immunogen specific allotype and isotype antibody responses in the nasal lavage and serum from subjects immunized with cationic liposome encapsulated recombinant Rv0164, Rv0831c, and Rv1324 combination at 2 and 4 weeks post immunization.

The titer of Rv1324 specific allotypes and isotypes in the serum and nasal lavage of i.n. cationic liposome encapsulated Rv1324 immunized mice was subsequently evaluated at 2 week time point and is depicted in FIG. 14.

Example 15

Figure 15:
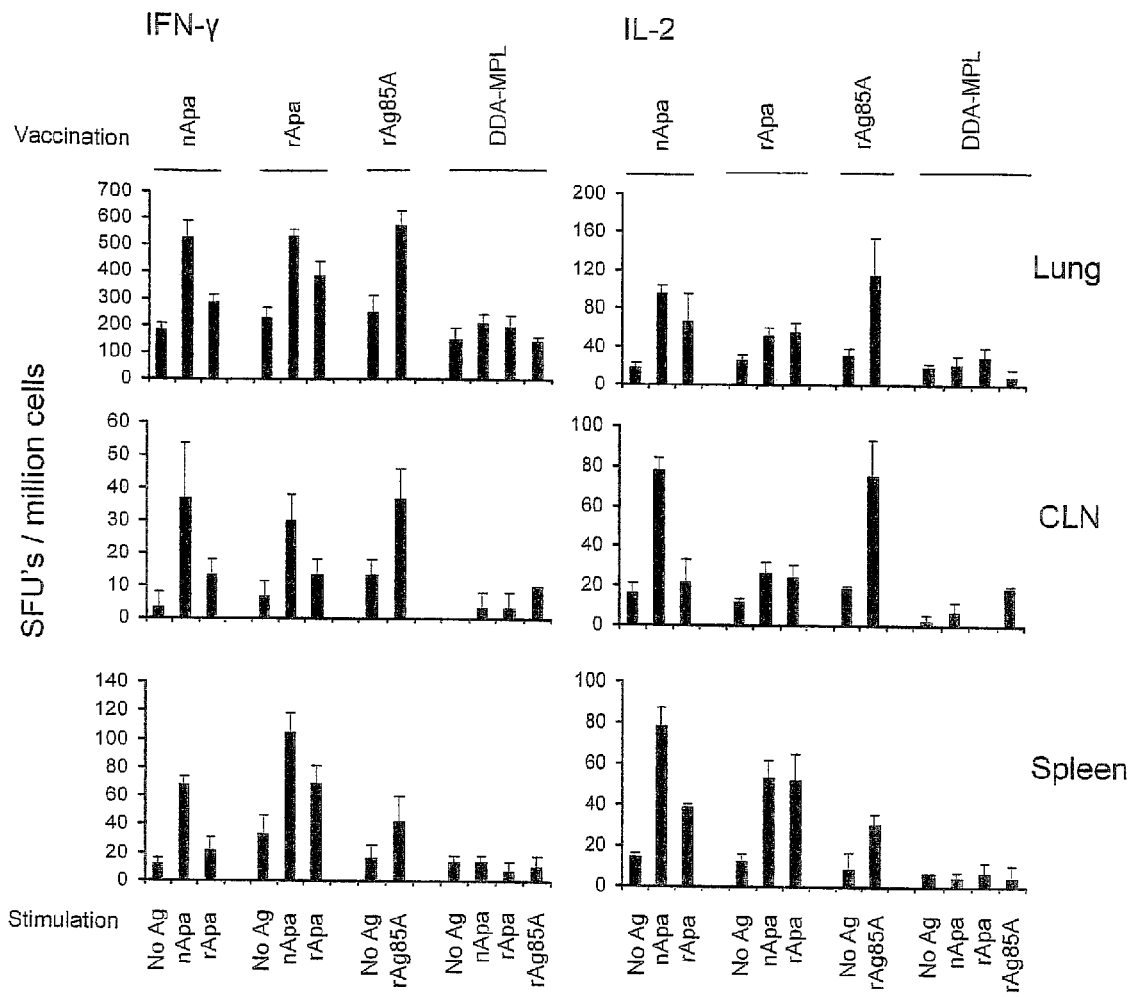
FIG. 15 represents the comparative ability of *M. tuberculosis* native Apa (nApa), recombinant APA (rApa), recombinant Ag85A (rAg85A) and control DDA-MPL adjuvant to induce Th1 response (IFN-γ and IL-2) in BALB/c mice immunized intranasally with respective protein subunit vaccine or DDA-MPL adjuvant alone for lung, cervical, lymph nodes (CLN) or spleen cells.
Figure 16:
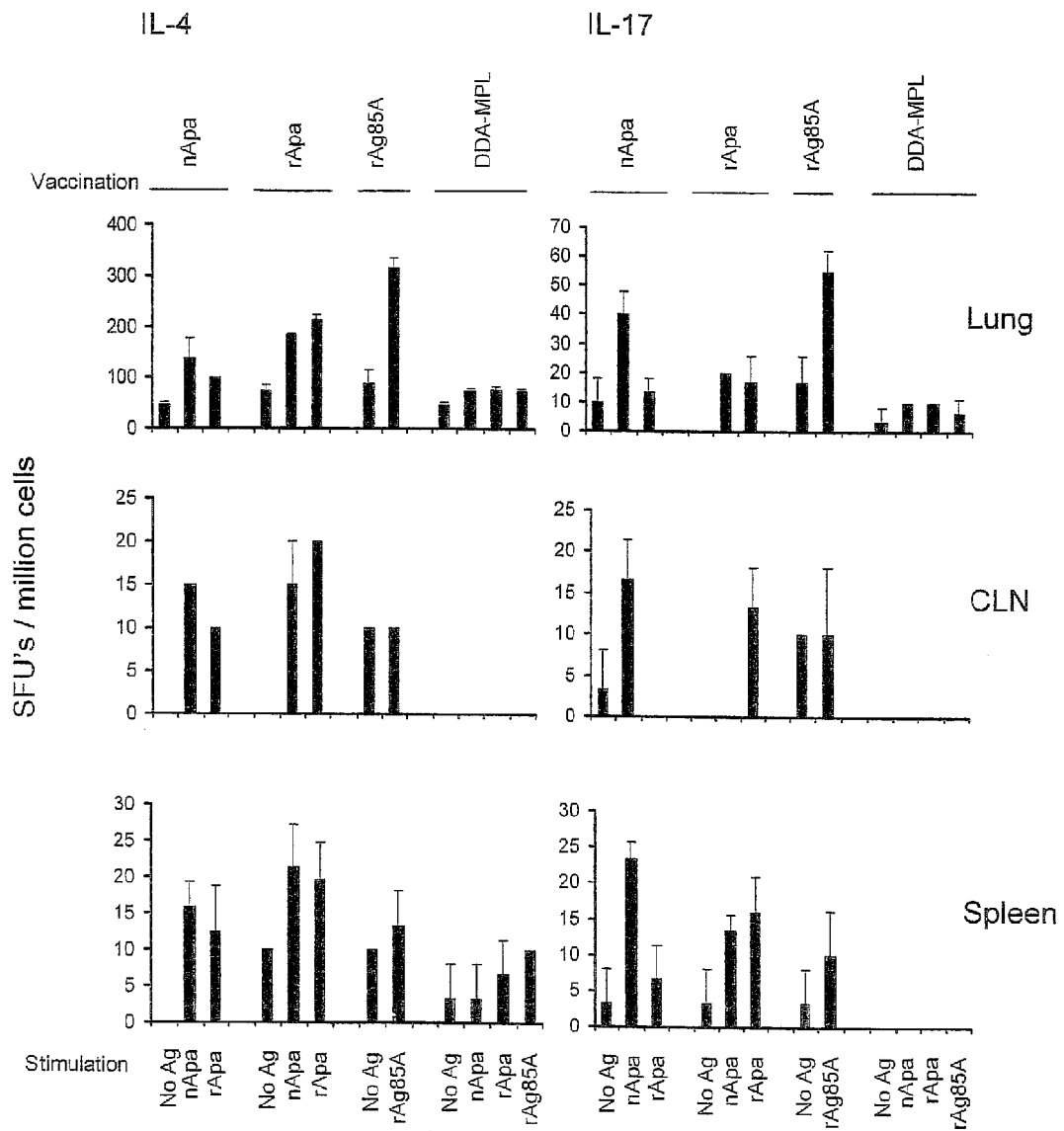
FIG. 16 represents the comparative ability of *M. tuberculosis* native Apa, recombinant APA, recombinant Ag85A and control DDA-MPL to induce Th2 or Th17 response in BALB/c mice immunized intranasally with respective protein subunit vaccine or DDA-MPL adjuvant alone for lung, CLN and spleen cells.
Figure 17:
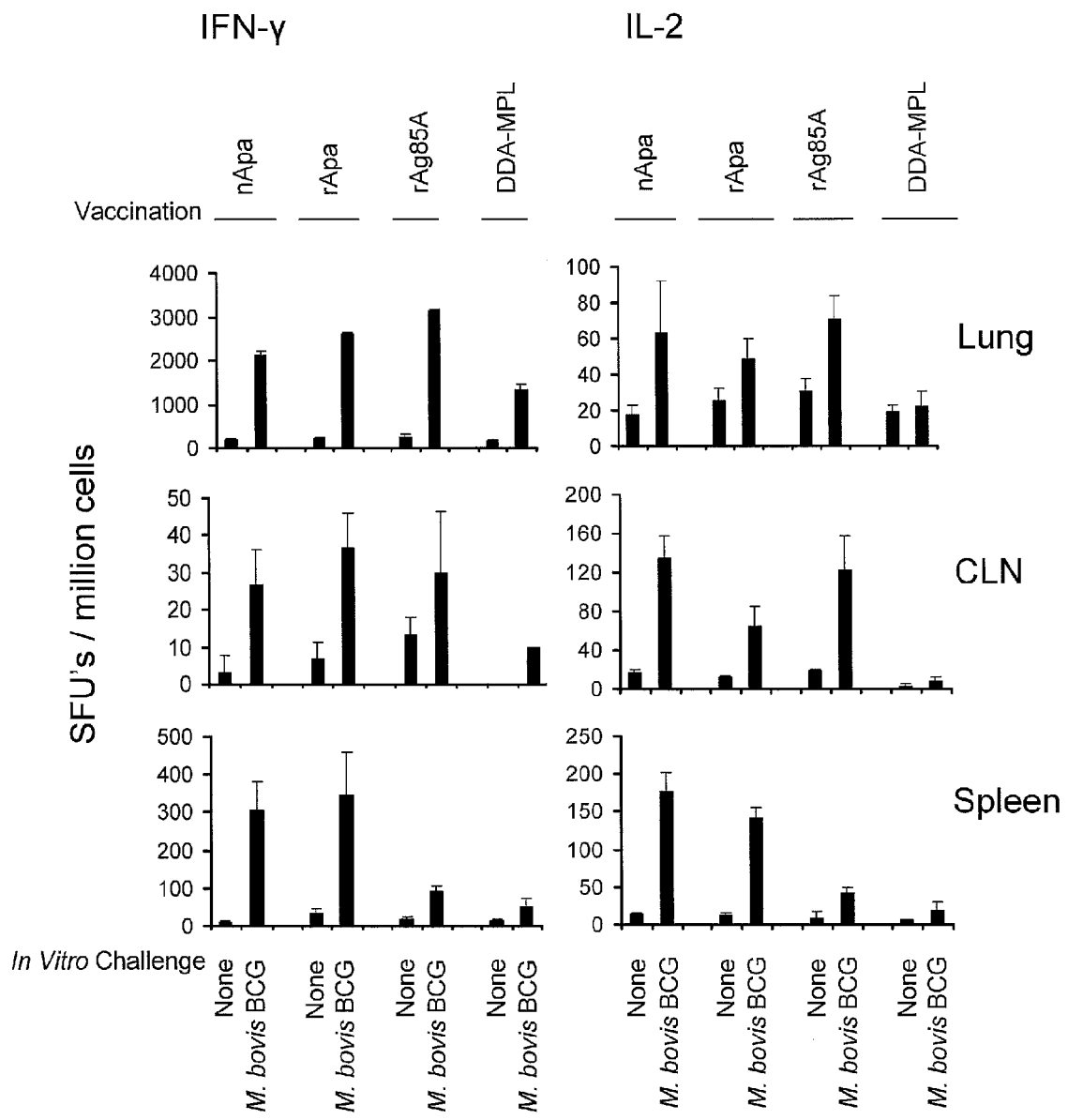
FIG. 17 represents the frequency of Th1 (IFN-γ and IL-2) cytokine-secreting cells in the lung, cervical lymph node (CLN), and spleen cell cultures of subunit and sham immunized mice following in vitro *M. bovis* BCG challenge at four weeks post-immunization in lung, CLN and spleen cell cultures.
Figure 18:
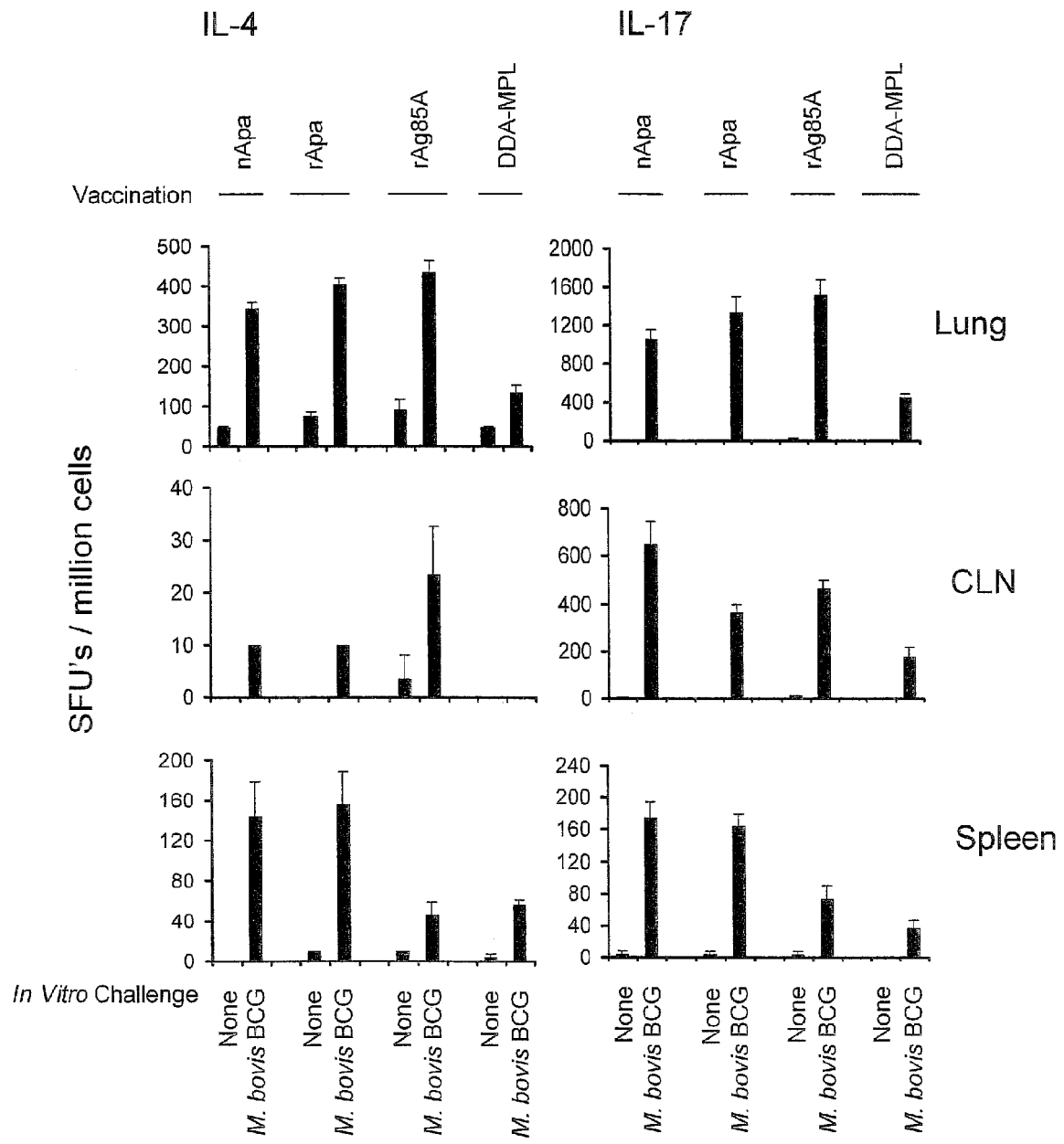
FIG. 18 represents the frequency of Th2 (IL-4) and Th17 (IL-17) cytokine-secreting cells in the lung, cervical lymph node (CLN), and spleen cell cultures of subunit and sham immunized mice following in vitro *M. bovis* BCG challenge at four weeks post-immunization.

Immunogenicity of Native and Recombinant Apa Based Experimental Subunit Vaccines in Mice For subunit vaccination, BALB/c mice were immunized by the intranasal route three times at 2-week intervals using 10 µg of either native *M. tuberculosis* Apa, recombinant *E. coli* expressed Apa or recombinant Ag85A individually [10 ug of each immunogen emulsified individually in Dimethyl-dioctadecyl-ammonium bromide (DDA; 250 μg/dose, Sigma-Aldrich, St. Louis, Mo.) and monophosphoryl lipid A (MPL derived from *Salmonella minnesota* Re 595; 25 μg/dose, Sigma-Aldrich, St. Louis, Mo.)]. MPL was first mixed with endotoxin-free sterile water (Burdick & Jackson, Muskegon, Mich.) containing 0.2% triethylamine (Fisher Scientific, Fair Lawn, N.J.). The mixture was heated in a 70° C. water bath for 30 s and then sonicated for 30 s. The heating and sonicating procedure was repeated twice. To prepare the emulsion, DDA was suspended in sterile water and a homogeneous dispersion of the powder was obtained by heating the suspension at 80° C. for 5-10 min in water bath. After cooling to room temperature, MPL and antigens were mixed with DDA just before use. The sham-immunized mice received PBS (pH 7.2) emulsified in DDA-MPL.

Following vaccination, mice were bled by cardiac puncture under anesthesia and sacrificed at 2 and 4 weeks post-immunization. Lungs, spleen and cervical lymph nodes (CLN) were aseptically removed and placed into RPMI 1640 supplemented with 100 IU $ml^{-1}$ penicillin, 50 μg $ml^{-1}$ streptomycin, 1 mM L-glutamine, 25 mM HEPES, 1 mM sodium pyruvate, $5\times10^{-5}$ M β-mercaptoethanol, vitamins and nonessential amino acids (Gibco-Invitrogen, Grand Island, N.Y.) and 10% endotoxin-tested heat-inactivated fetal calf serum (FCS; Atlas Biologicals, Fort Collins, Colo.). In each case, the respective lymphoid or extra-lymphoid organs were pooled from 4 mice for each treatment group and cells were extracted for analysis of in vitro *M. tuberculosis* antigen-specific cellular responses. Antigen-specific antibody responses were evaluated using pooled nasal lavage and serum collected from each treatment group.

To isolate lung cells, mice were bled by cardiac puncture under anesthesia and their lungs were perfused via the right ventricle with PBS containing 10 U $ml^{-1}$ heparin to remove intravascular leukocytes. The lungs were then perfused with an enzyme mixture containing 1 mg/ml collagenase type IV (Sigma-Aldrich, St. Louis, Mo.) and 25 U $ml^{-1}$ DNase (Roche, Penzberg, Germany) in supplemented RPMI and sliced into small pieces in a sterile dish and the fragments were incubated in the enzyme mixture at 37° C. for 1 h. The digested lung fragments were pressed with a 5 ml syringe plunger through a 70-μm pore size cell strainer (BD Falcon, Bedford, Mass.) to obtain a single cell suspension and erythrocytes were lysed with RBC lysis buffer (eBioscience, San Diego, Calif.) for 4-5 min at room temperature. The lung cells were washed, recovered by centrifugation, and resuspended in supplemented RPMI for counting using the trypan blue dye exclusion method. The single cell suspensions of spleen and lymph nodes were obtained by gently grinding the respective organs through a 70-μm cell strainer into 10-20 ml supplemented RPMI. The cell suspensions were centrifuged at 300×g for 10 min and the erythrocytes were removed by treatment with RBC lysis buffer when necessary. Cells were washed several times with fresh RPMI and the cell concentration was adjusted accordingly.

Commercially available interferon (IFN)-γ, IL-2, IL-4 (Mouse ELISPOT set; BD-Biosciences, San Diego, Calif.) and IL-17 (Mouse ELISPOT set, eBioscience) kits were used to enumerate frequencies of *M. tuberculosis* antigen-specific cells according to the manufacturer's protocol. In brief, 96 well ELISPOT plates were coated with 100 μl of 5 μg $ml^{-1}$ capture antibody in PBS (pH 7.2) and incubated overnight at 4° C. Free binding sites were blocked with 200 μl of supplemented RPMI containing 10% FCS for 2 h at room temperature. Cell concentration was adjusted to $1\times10^6$ and $2\times10^6$ cells $ml^{-1}$ for all sites and added to appropriate wells. No BM-derived DCs or macrophages were added to supplement the antigen presenting cells already present in the cell suspension as described previously for antigenicity or immunogenicity studies. For each treatment group, cells were stimulated in triplicate with either 10 μg $ml^{-1}$ of individual purified *M. tuberculosis* antigens, WCL, Concanavalin A (Con-A; Sigma-Aldrich, St. Louis, Mo.), or medium alone in a 100 μl volume. After 36 h of incubation at 37° C. in a humidified atmosphere containing 5% $CO_2$, the unattached cells were aspirated from the well and the remaining cells were lysed with distilled water. The wells were washed again with PBS containing 0.05% Tween-20 (PBS-T) and the site of cytokine secretion was detected with a biotin-labeled anti-mouse cytokine antibody and horseradish peroxidase-conjugated streptavidin. The enzyme reaction was developed using 3-amino-9-ethylcarbazole (AEC) substrate reagent set (BD-Bioscience, San Diego, Calif.). The number of spot forming units (SFUs) per well were counted automatically using an ELISPOT reader (Cellular Technology Limited, Cleveland, Ohio).

Immunization of mice with either native or recombinant Apa in DDA-MPL adjuvant induced comparable Th1 (IFN-γ and IL-2) (FIG. 15), Th2 (IL-4) and Th17 (IL-17) (FIG. 16)

cytokine responses in lungs, cervical lymph nodes (CLN), and spleen as evaluated by ELISPOT assay at 4 weeks post-immunization. In FIG. 15, the comparative ability of *M. tuberculosis* native Apa (nApa), recombinant APA (RApa), recombinant Ag85A (rAg85A), and control DDA-MPL adjuvent to induce Th1 response (IFN-γ and IL-2) in BALB/c mice immunized intranasally with respective protein subunit vaccine or DDA-MPL adjuvant alone for lung, cervical, lymph nodes (CLN) or spleen cells. Intranasal rAg85A-DDA-MPL subunit vaccination was used as a positive control for evaluation of immunogenicity of native or recombinant Apa. Four weeks post immunization (time point to be used for *M. tuberculosis* challenge of vaccinated mice), the frequencies of antigen-specific Th1 (IFN-γ and IL-2) cytokine-secreting cells in lungs, cervical lymph nodes (CLN), and spleen were enumerated by ELISPOT assay and expressed as spot forming units (SFUs)/million cells of organ. The results are presented as means±standard deviation of three to six determinations. In FIG. 16, the comparative ability of *M. tuberculosis* native Apa, recombinant APA, recombinant Ag85A and control DDA-MPL to induce Th2 or Th17 response in BALB/c mice immunized intranasally with respective protein subunit vaccine or DDA-MPL adjuvant alone for lung, CLN and spleen cells. Four weeks post immunization the frequencies of antigen-specific Th2 (IL-4) and Th17 (IL-17) cytokine-secreting cells in lungs, cervical lymph nodes (CLN), and spleen were enumerated by ELISPOT assay and expressed as spot forming units (SFUs)/million cells of organ. The results are presented as means±standard deviation of three to six determinations. The T-cell responses induced by native or recombinant Apa were also comparable with those induced by rAg85A immunization. No difference was also observed in three vaccine immunized groups to induce T-cell (Th1, Th2 and Th17) responses following in vitro live *M. bovis* BCG stimulation of respective lung, CLN and spleen cell cultures indicating that three vaccine group might induce similar T-cell cytokine responses following *M. tuberculosis* encounter or in vivo experimental challenge (FIGS. 17 and 18). In FIG. 17, the frequency of Th1 (IFN-γ and IL-2) cytokine-secreting cells in the lung, cervical lymph node (CLN), and spleen cell cultures of subunit and sham immunized mice following in vitro *M. bovis* BCG challenge at four weeks post-immunization in lung, CLN and spleen cell cultures. Live *M. Bovis* BCG Copenhagen CFUs were used to stimulate respective organ cell culture (1:10 ratio) without antibiotic for 36 hr. IFN-γ and IL-2 secreting cells were enumerated by ELISPOT assay and expressed as spot forming units (SFUs)/million cells of organ. The results are presented as means±standard deviation of three to six determinations.

All reagents necessary for using the instant invention are available from sources known in the art or are readily synthesized by techniques described herein or by methods recognized in the art.

References cited or otherwise present herein are indicative of the level of skill in the art to which the invention pertains. These references are hereby incorporated by reference to the same extent as if each individual reference was explicitly and individually incorporated herein.

REFERENCE LIST

1. Anonymous. 2006. Emergence of *Mycobacterium tuberculosis* with extensive resistance to second-line drugs—worldwide, 2000-2004. Centers for Disease Control and Prevention. MMWR 55:301-305.
2. Agger, E. M., and P. Andersen. 2002. A novel TB vaccine; towards a strategy based on our understanding of BCG failure. Vaccine 21:7-14.
3. Andersen, P., and T. M. Doherty. 2005. The success and failure of BCG—implications for a novel tuberculosis vaccine. Nat Rev Microbiol 3:656-662.
4. Arulanandam, B. P., R. H. Raeder, J. G. Nedrud, D. J. Bucher, J. Le, and D. W. Metzger. 2001. IgA immunodeficiency leads to inadequate Th cell priming and increased susceptibility to influenza virus infection. J Immunol 166: 226-231.
5. Asanuma, H., A. H. Thompson, T. Iwasaki, Y. Sato, Y. Inaba, C. Aizawa, T. Kurata, and S. Tamura. 1997. Isolation and characterization of mouse nasal-associated lymphoid tissue. J Immunol Methods 202:123-131.
6. Beatty, W. L., and D. G. Russell. 2000. Identification of mycobacterial surface proteins released into subcellular compartments of infected macrophages. Infect Immun 68:6997-7002.
7. Carpenter, Z. K., E. D. Williamson, and J. E. Eyles. 2005. Mucosal delivery of microparticle encapsulated ESAT-6 induces robust cell-mediated responses in the lung milieu. J Control Release 104:67-77.
8. Castanon-Arreola, M., Y. Lopez-Vidal, C. Espitia-Pinzon, and R. Hernandez-Pando. 2005. A new vaccine against tuberculosis shows greater protection in a mouse model with progressive pulmonary tuberculosis. Tuberculosis (Edinburgh, Scotland) 85:115-126.
9. Chen, L., J. Wang, A. Zganiacz, and Z. Xing. 2004. Single intranasal mucosal *Mycobacterium bovis* BCG vaccination confers improved protection compared to subcutaneous vaccination against pulmonary tuberculosis. Infect Immun 72:238-246.
10. D'Souza, S., V. Rosseels, O. Denis, A. Tanghe, N. De Smet, F. Jurion, K. Palfliet, N. Castiglioni, A. Vanonckelen, C. Wheeler, and K. Huygen. 2002. Improved tuberculosis DNA vaccines by formulation in cationic lipids. Infect Immun 70:3681-3688.
11. Denis, O., E. Lozes, and K. Huygen. 1997. Induction of cytotoxic T-cell responses against culture filtrate antigens in *Mycobacterium bovis bacillus* Calmette-Guerin-infected mice. Infect Immun 65:676-684.
12. Di Rosa, F., and R. Pabst. 2005. The bone marrow: a nest for migratory memory T cells. Trends Immunol 26:360-366.
13. Dietrich, J., C. Andersen, R. Rappuoli, T. M. Doherty, C. G. Jensen, and P. Andersen. 2006. Mucosal administration of Ag85B-ESAT-6 protects against infection with *Mycobacterium tuberculosis* and boosts prior *bacillus* Calmette-Guerin immunity. J Immunol 177:6353-6360.
14. Dobos, K. M., K. H. Khoo, K. M. Swiderek, P. J. Brennan, and J. T. Belisle. 1996. Definition of the full extent of glycosylation of the 45-kilodalton glycoprotein of *Mycobacterium tuberculosis*. J Bacteriol 178:2498-2506.
15. Falero-Diaz, G., S. Challacombe, D. Banerjee, G. Douce, A. Boyd, and J. Ivanyi. 2000. Intranasal vaccination of mice against infection with *Mycobacterium tuberculosis*. Vaccine 18:3223-3229.
16. Fattorini, L., R. Creti, R. Nisini, R. Pietrobono, Y. Fan, A. Stringaro, G. Arancia, O. Serlupi-Crescenzi, E. Iona, and G. Orefici. 2002. Recombinant GroES in combination with CpG oligodeoxynucleotides protects mice against *Mycobacterium avium* infection. J Med Microbiol 51:1071-1079.
17. Ferraz, J. C., E. Stavropoulos, M. Yang, S. Coade, C. Espitia, D. B. Lowrie, M. J. Colston, and R. E. Tascon. 2004. A heterologous DNA priming-*Mycobacterium bovis*

BCG boosting immunization strategy using mycobacterial Hsp70, Hsp65, and Apa antigens improves protection against tuberculosis in mice. Infect Immun 72:6945-6950.
18. Giri, P. K., S. B. Sable, I. Verma, and G. K. Khuller. 2005. Comparative evaluation of intranasal and subcutaneous route of immunization for development of mucosal vaccine against experimental tuberculosis. FEMS Immunol Med Microbiol 45:87-93.
19. Giri, P. K., I. Verma, and G. K. Khuller. 2006. Enhanced immunoprotective potential of *Mycobacterium tuberculosis* Ag85 complex protein based vaccine against airway *Mycobacterium tuberculosis* challenge following intranasal administration. FEMS Immunol Med Microbiol 47:233-241.
20. Goonetilleke, N. P., H. McShane, C. M. Hannan, R. J. Anderson, R. H. Brookes, and A. V. Hill. 2003. Enhanced immunogenicity and protective efficacy against *Mycobacterium tuberculosis* of bacille Calmette-Guerin vaccine using mucosal administration and boosting with a recombinant modified vaccinia virus Ankara. J Immunol 171: 1602-1609.
21. Grode, L., P. Seiler, S. Baumann, J. Hess, V. Brinkmann, A. Nasser Eddine, P. Mann, C. Goosmann, S. Bandermann, D. Smith, G. J. Bancroft, J. M. Reyrat, D. van Soolingen, B. Raupach, and S. H. Kaufmann. 2005. Increased vaccine efficacy against tuberculosis of recombinant *Mycobacterium Bovis* bacille Calmette-Guerin mutants that secrete listeriolysin. J Clin Invest 115:2472-2479.
22. Grover, A., M. F. Ahmed, B. Singh, I. Verma, P. Sharma, and G. K. Khuller. 2006. A multivalent combination of experimental antituberculosis DNA vaccines based on Ag85B and regions of difference antigens. Microbes Infect/Institut Pasteur 8:2390-2399.
23. Hagiwara, Y., J. R. McGhee, K. Fujihashi, R. Kobayashi, N. Yoshino, K. Kataoka, Y. Etani, M. N. Kweon, S. Tamura, T. Kurata, Y. Takeda, H. Kiyono, and K. Fujihashi. 2003. Protective mucosal immunity in aging is associated with functional CD4+ T cells in nasopharyngeal-associated lymphoreticular tissue. J Immunol 170:1754-1762.
24. Haile, M., B. Hamasur, T. Jaxmar, D. Gavier-Widen, M. A. Chambers, B. Sanchez, U. Schroder, G. Kallenius, S. B. Svenson, and A. Pawlowski. 2005. Nasal boost with adjuvanted heat-killed BCG or arabinomannan-protein conjugate improves primary BCG-induced protection in C57BL/6 mice. Tuberculosis (Edinburgh, Scotland) 85:107-114.
25. Hamasur, B., M. Haile, A. Pawlowski, U. Schroder, A. Williams, G. Hatch, G. Hall, P. Marsh, G. Kallenius, and S. B. Svenson. 2003. *Mycobacterium tuberculosis* arabinomannan-protein conjugates protect against tuberculosis. Vaccine 21:4081-4093.
26. Horn, C., A. Namane, P. Pescher, M. Riviere, F. Romain, G. Puzo, O. Barzu, and G. Marchal. 1999. Decreased capacity of recombinant 45/47-kDa molecules (Apa) of *Mycobacterium tuberculosis* to stimulate T lymphocyte responses related to changes in their mannosylation pattern. J Biol Chem 274:32023-32030.
27. Horwitz, M. A., G. Harth, B. J. Dillon, and S. Maslesa-Galic. 2000. Recombinant *bacillus* calmette-guerin (BCG) vaccines expressing the *Mycobacterium tuberculosis* 30-kDa major secretory protein induce greater protective immunity against tuberculosis than conventional BCG vaccines in a highly susceptible animal model. Proc Natil Acad Sci U S A 97:13853-13858.
28. Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte/macrophage colony-stimulating factor. J Exp Med 176: 1693-1702.
29. Kallenius, G., A. Pawlowski, P. Brandtzaeg, and S. Svenson. 2007. Should a new tuberculosis vaccine be administered intranasally? Tuberculosis (Edinburgh, Scotland).
30. Kamath, A. T., C. G. Feng, M. Macdonald, H. Briscoe, and W. J. Britton. 1999. Differential protective efficacy of DNA vaccines expressing secreted proteins of *Mycobacterium tuberculosis*. Infect Immun 67:1702-1707.
31. Kaufmann, S. H. 2006. Envisioning future strategies for vaccination against tuberculosis. Nat Rev Immunol 6:699-704.
32. Kawanishi, H., and J. Kiely. 1989. Immune-related alterations in aged gut-associated lymphoid tissues in mice. Dig Dis Sci 34:175-184.
33. Kumar, P., R. R. Amara, V. K. Challu, V. K. Chadda, and V. Satchidanandam. 2003. The Apa protein of *Mycobacterium tuberculosis* stimulates gamma interferon-secreting CD4+ and CD8+ T cells from purified protein derivative-positive individuals and affords protection in a guinea pig model. Infect Immun 71:1929-1937.
34. Kuroda, K., E. J. Brown, W. B. Telle, D. G. Russell, and T. L. Ratliff. 1993. Characterization of the internalization of *bacillus* Calmette-Guerin by human bladder tumor cells. J Clinical Invest 91:69-76.
35. Lefrancois, L., and D. Masopust. 2002. T cell immunity in lymphoid and non-lymphoid tissues. Curr Opin Immunol 14:503-508.
36. McShane, H., A. A. Pathan, C. R. Sander, S. M. Keating, S. C. Gilbert, K. Huygen, H. A. Fletcher, and A. V. Hill. 2004. Recombinant modified vaccinia virus Ankara expressing antigen 85A boosts BCG-primed and naturally acquired antimycobacterial immunity in humans. Nat Med 10:1240-1244.
37. Mustafa, A. S., K. E. Lundin, and F. Oftung. 1993. Human T cells recognize mycobacterial heat shock proteins in the context of multiple HLA-DR molecules: studies with healthy subjects vaccinated with *Mycobacterium bovis* BCG and *Mycobacterium leprae*. Infect Immun 61:5294-5301.
38. Parida, S. K., K. Huygen, B. Ryffel, and T. Chakraborty. 2005. Novel Bacterial Delivery System with Attenuated *Salmonella typhimurium* Carrying Plasmid Encoding Mtb Antigen 85A for Mucosal Immunization: Establishment of Proof of Principle in TB Mouse Model. Ann N Y Acad Sci 1056:366-378.
39. Quiding-Jarbrink, M., I. Nordstrom, G. Granstrom, A. Kilander, M. Jertborn, E. C. Butcher, A. I. Lazarovits, J. Holmgren, and C. Czerkinsky. 1997. Differential expression of tissue-specific adhesion molecules on human circulating antibody-forming cells after systemic, enteric, and nasal immunizations. A molecular basis for the compartmentalization of effector B cell responses. J Clin Invest 99:1281-1286.
40. Reinhardt, R. L., A. Khoruts, R. Merica, T. Zell, and M. K. Jenkins. 2001. Visualizing the generation of memory CD4 T cells in the whole body. Nature 410:101-105.
41. Rodriguez, A., A. Tjarnlund, J. Ivanji, M. Singh, I. Garcia, A. Williams, P. D. Marsh, M. Troye-Blomberg, and C. Fernandez. 2005. Role of IgA in the defense against respiratory infections IgA deficient mice exhibited increased susceptibility to intranasal infection with *Mycobacterium bovis* BCG. Vaccine 23:2565-2572.
42. Romain, F., C. Horn, P. Pescher, A. Namane, M. Riviere, G. Puzo, O. Barzu, and G. Marchal. 1999. Deglycosylation of the 45/47-kilodalton antigen complex of *Mycobacte-*

*rium tuberculosis* decreases its capacity to elicit in vivo or in vitro cellular immune responses. Infect Immun 67:5567-5572.

43. Romain, F., A. Laqueyrerie, P. Militzer, P. Pescher, P. Chavarot, M. Lagranderie, G. Auregan, M. Gheorghiu, and G. Marchal. 1993. Identification of a *Mycobacterium Bovis* BCG 45/47-kilodalton antigen complex, an immunodominant target for antibody response after immunization with living bacteria. Infect Immun 61:742-750.

44. Rook, G. A., K. Dheda, and A. Zumla. 2005. Do successful tuberculosis vaccines need to be immunoregulatory rather than merely Th1-boosting? Vaccine 23:2115-2120.

45. Rudin, A., E. L. Johansson, C. Bergquist, and J. Holmgren. 1998. Differential kinetics and distribution of antibodies in serum and nasal and vaginal secretions after nasal and oral vaccination of humans. Infect Immun 66:3390-3396.

46. Sable, S. B., D. Goyal, I. Verma, D. Behera, and G. K. Khuller. 2007. Lung and blood mononuclear cell responses of tuberculosis patients to mycobacterial proteins. Eur Respir J 29:337-346.

47. Sable, S. B., I. Verma, and G. K. Khuller. 2005. Multicomponent antituberculous subunit vaccine based on immunodominant antigens of *Mycobacterium tuberculosis*. Vaccine 23:4175-4184.

48. Sereinig, S., M. Stukova, N. Zabolotnyh, B. Ferko, C. Kittel, J. Romanova, T. Vinogradova, H. Katinger, O. Kiselev, and A. Egorov. 2006. Influenza virus NS vectors expressing the *Mycobacterium tuberculosis* ESAT-6 protein induce CD4+ Th1 immune response and protect animals against tuberculosis challenge. Clin Vaccine Immunol 13:898-904.

49. Silva, C. L., M. F. Silva, R. C. Pietro, and D. B. Lowrie. 1994. Protection against tuberculosis by passive transfer with T-cell clones recognizing mycobacterial heat-shock protein 65. Immunology 83:341-346.

50. Skeiky, Y. A., M. R. Alderson, P. J. Ovendale, J. A. Guderian, L. Brandt, D. C. Dillon, A. Campos-Neto, Y. Lobet, W. Dalemans, I. M. Orme, and S. G. Reed. 2004. Differential immune responses and protective efficacy induced by components of a tuberculosis polyprotein vaccine, Mtb72F, delivered as naked DNA or recombinant protein. J Immunol 172:7618-7628.

51. Smith, C., and C. Cheers. 2005. Synergism between active listeriolysin O and dimethyldioctadecylammonium bromide to activate CD8(+) T cells. Vaccine 23:4481-4488.

52. Sullivan, V. J., J. A. Mikszta, P. Laurent, J. Huang, and B. Ford. 2006. Noninvasive delivery technologies: respiratory delivery of vaccines. Expert Opin Drug Deliv 3:87-95.

53. Takahashi, H., K. Sasaki, M. Takahashi, N. Shigemori, S. Honda, H. Arimitsu, S. Ochi, N. Ohara, and T. Tsuji. 2006. Mutant *Escherichia coli* enterotoxin as a mucosal adjuvant induces specific Th1 responses of CD4+ and CD8+ T cells to nasal killed-*bacillus* calmette-guerin in mice. Vaccine 24:3591-3598.

54. Van Savage, J., M. D. Decker, K. M. Edwards, S. H. Sell, and D. T. Karzon. 1990. Natural history of pertussis antibody in the infant and effect on vaccine response. J Infect Dis 161:487-492.

55. Wang, J., L. Thorson, R. W. Stokes, M. Santosuosso, K. Huygen, A. Zganiacz, M. Hitt, and Z. Xing. 2004. Single mucosal, but not parenteral, immunization with recombinant adenoviral-based vaccine provides potent protection from pulmonary tuberculosis. J Immunol 173:6357-6365.

56. Weinrich Olsen, A., L. A. van Pinxteren, L. Meng Okkels, P. Birk Rasmussen, and P. Andersen. 2001. Protection of mice with a tuberculosis subunit vaccine based on a fusion protein of antigen 85b and esat-6. Infect Immun 69:2773-2778.

57. Williams, A., R. Reljic, I. Naylor, S. O. Clark, G. Falero-Diaz, M. Singh, S. Challacombe, P. D. Marsh, and J. Ivanyi. 2004. Passive protection with immunoglobulin A antibodies against tuberculous early infection of the lungs. Immunology 111:328-333.

58. Worku, S., and D. F. Hoft. 2003. Differential effects of control and antigen-specific T cells on intracellular mycobacterial growth. Infect Immun 71:1763-1773.

59. Zhao, W., J. S. Schorey, M. Bong-Mastek, J. Ritchey, E. J. Brown, and T. L. Ratliff. 2000. Role of a *bacillus* Calmette-Guerin fibronectin attachment protein in BCG-induced antitumor activity. Int J Cancer 86:83-88.

Andersen, C. S., J. Dietrich, E. M. Agger, N. Y. Lycke, K. Lovgren, and P.

60. Andersen. 2007. The combined CTA1-DD/ISCOMs vector is an effective intranasal adjuvant for boosting prior *Mycobacterium Bovis* BCG immunity to *Mycobacterium tuberculosis*. Infection and immunity 75:408-416.
61. Brandt, L., M. Elhay, I. Rosenkrands, E. B. Lindblad, and P. Andersen. 2000. ESAT-6 subunit vaccination against *Mycobacterium tuberculosis*. Infection and immunity 68:791-795.
62. Fine, P. E. 2001. BCG: the challenge continues. Scandinavian journal of infectious diseases 33:243-245.
63. Fine, P. E. 1995. Variation in protection by BCG: implications of and for heterologous immunity. Lancet 346: 1339-1345.
64. Haile, M., U. Schroder, B. Hamasur, A. Pawlowski, T. Jaxmar, G. Kallenius, and S. B. Svenson. 2004. Immunization with heat-killed *Mycobacterium bovis* bacille Calmette-Guerin (BCG) in Eurocine L3 adjuvant protects against tuberculosis. Vaccine 22:1498-1508.
65. Hesseling, A. C., B. J. Marais, R. P. Gie, H. S. Schaaf, P. E. Fine, P. Godfrey-Faussett, and N. Beyers. 2007. The risk of disseminated Bacille Calmette-Guerin (BCG) disease in HIV-infected children. Vaccine 25:14-18.
66. Lim, J. H., H. J. Kim, K. S. Lee, E. K. Jo, C. H. Song, S. B. Jung, S. Y. Kim, J. S. Lee, T. H. Paik, and J. K. Park. 2004. Identification of the new T-cell-stimulating antigens from *Mycobacterium tuberculosis* culture filtrate. FEMS microbiology letters 232:51-59.
67. Oganesyan, N., S. H. Kim, and R. Kim. September 2004. On-column protein refolding for crystallization. PharmGenomics: 22-25.
68. Orme, I. M. 2006. Preclinical testing of new vaccines for tuberculosis: a comprehensive review. Vaccine 24:2-19.
69. Sable, S. B., M. Kalra, I. Verma, and G. K. Khuller. 2007. Tuberculosis subunit vaccine design: the conflict of antigenicity and immunogenicity. Clinical immunology (Orlando, Fla. 122:239-251.
70. Sable, S. B., R. Kumar, M. Kalra, I. Verma, G. K. Khuller, K. Dobos, and J. T. Belisle. 2005. Peripheral blood and pleural fluid mononuclear cell responses to low-molecular-mass secretory polypeptides of *Mycobacterium tuberculosis* in human models of immunity to tuberculosis. Infection and immunity 73:3547-3558.
71. Sable, S. B., I. Verma, D. Behera, and G. K. Khuller. 2005. Human immune recognition-based multicomponent subunit vaccines against tuberculosis. Eur Respir J 25:902-910.
72. Santosuosso, M., S. McCormick, X. Zhang, A. Zganiacz, and Z. Xing. 2006. Intranasal boosting with an adenovirus-vectored vaccine markedly enhances protection by parenteral *Mycobacterium bovis* BCG immunization against pulmonary tuberculosis. Infection and immunity 74:4634-4643.

73. Xu, Y., Zhu, B., Wang, Q., Chen, J., Qie, Y., Wang, J., Wang, H., Wang, B., and Wang, H. 2007 Recombinant BCG coexpressing Ag85B, ESAT-6 and mouse-IFN-γ confers effective protection against *Mycobacterium tuberculosis* in C57BL/6 mice *FEMS Immunology and Medical Microbiology,* 51:480-487

The invention claimed is:

1. A vaccine comprising:
   a non-glycosylated *M. tuberculosis* polypeptide of Rv1324, or a combination of *M. tuberculosis* polypeptides of Ag85A, Ag85B, MPT-64, Pst-S1, Apa, GroES, GroEL, Dnak, non-glycosylated Rv1324, and CFP10; and
   an adjuvant.

2. The vaccine of claim 1 wherein said polypeptide is recombinant.

3. The vaccine of claim 1 wherein said polypeptide is a fusion peptide vaccine comprising Apa, and non-glycosylated Rv1324.

4. The vaccine of claim 1 wherein said polypeptide consists of non-glycosylated Rv1324.

5. The vaccine of claim 1 wherein said polypeptide further comprises a tag suitable for purification.

6. The vaccine of claim 1 wherein said adjuvant is dimethyl dioctadecyl-ammonium bromide (DDA); monophosphoryl lipid A (MPL); LTK63, lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles illustratively including calcium phosphate nanoparticles, a combination of soybean oil, emulsifying agents, and ethanol to form a nanoemulsion; AS04, ZADAXIN, or combinations thereof.

7. The vaccine of claim 1 further comprising an emulsifying agent or an encapsulating agent.

8. The vaccine of claim 7 wherein said emulsification agent is supramolecular biovectors (SMBV), nanoparticles, liposomes, or combinations thereof.

9. A pharmaceutical package comprising:
   the vaccine of claim 1 alone or in combination with BCG vaccine;
   an emulsification agent; and
   an adjuvant.

10. The pharmaceutical package of claim 9 wherein said adjuvant is dimethyl dioctadecyl-ammonium bromide (DDA); monophosphoryl lipid A (MPL); LTK63, lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles illustratively including calcium phosphate nanoparticles, combination of soybean oil, emulsifying agents, and ethanol to form a nanoemulsion; AS04, ZADAXIN, or combinations thereof.

11. The pharmaceutical package of claim 10 wherein said emulsification agent is supramolecular biovectors (SMBV), nanoparticles, liposomes, or combinations thereof.

12. A process of creating an immune response in subject cell tissue comprising administering to a subject a therapeutically or prophylactically effective amount of a first vaccine of the vaccine of claim 1.

13. The process of claim 12 further comprising administering a second vaccine.

14. The process of claim 13 wherein said second vaccine is the vaccine of claim 1, BCG, or combinations thereof.

15. The process of claim 13 wherein administering said first vaccine is prior to administering said second vaccine.

16. The process of claim 13 wherein said administering said first vaccine is subsequent to administering said second vaccine and said second vaccine is BCG.

17. The process of claim 13 wherein said administering said first vaccine is simultaneous with said second vaccine.

18. The process of claim 12 wherein said administering said first vaccine is after the subject cell tissue is exposed to *M. tuberculosis*.

* * * * *